US009447166B2

(12) United States Patent
Ambati et al.

(10) Patent No.: US 9,447,166 B2
(45) Date of Patent: Sep. 20, 2016

(54) COMPOSITIONS AND METHODS FOR THE INTRACELLULAR DISRUPTION OF VEGF AND VEGFR-2 BY INTRACEPTORS

(71) Applicants: Balamurali Ambati, Sandy, UT (US); Nirbhai Singh, Augusta, GA (US); Shivan Amin, Martinez, GA (US)

(72) Inventors: Balamurali Ambati, Sandy, UT (US); Nirbhai Singh, Augusta, GA (US); Shivan Amin, Martinez, GA (US)

(73) Assignees: Medical College of Georgia Research Institute, Augusta, GA (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 14/231,629

(22) Filed: Mar. 31, 2014

(65) Prior Publication Data

US 2014/0329888 A1 Nov. 6, 2014

Related U.S. Application Data

(63) Continuation of application No. 13/540,495, filed on Jul. 2, 2012, now abandoned, which is a continuation of application No. 11/814,890, filed as application No. PCT/US2006/002684 on Jan. 26, 2006, now Pat. No. 8,211,864.

(60) Provisional application No. 60/647,224, filed on Jan. 26, 2005.

(51) Int. Cl.

| A61K 31/70 | (2006.01) |
|---|---|
| C07H 21/04 | (2006.01) |
| C07K 14/71 | (2006.01) |
| C07K 5/11 | (2006.01) |
| A01K 67/00 | (2006.01) |
| A61K 38/00 | (2006.01) |

(52) U.S. Cl.
CPC ............. *C07K 14/71* (2013.01); *C07K 5/1019* (2013.01); *A61K 38/00* (2013.01); *C07K 2319/04* (2013.01)

(58) Field of Classification Search
CPC ... C07K 14/71; C07K 2319/04; A61K 48/00
USPC .......................................... 514/44; 536/23.4
See application file for complete search history.

(56) References Cited

U.S. PATENT DOCUMENTS

| 6,375,929 B1 * | 4/2002 | Thomas et al. ................ 424/9.2 |
| 8,211,864 B2 | 7/2012 | Ambati et al. |

FOREIGN PATENT DOCUMENTS

WO   WO 2006/001888   *   1/2006

OTHER PUBLICATIONS

Singh et al. Flt-1 intrareceptors inhibit hypoxia-induced VEGF expression in vitro and corneal neovascularization in vivo. Invest. Ophthalmol. Vis. Sci. 46:1647-1652, 2005.*

Genbank Acession No. AF063657, Dec. 2004.
Abad, et al.; 2003; "Novel Interfering Bifunctional Molecules Against the CCR5 Coreceptor Are Efficient Inhibitors of HIV-1 Infection;" Mol. Ther. 8 (3) 475-484.
Aiello et al.; 1995,; "Suppression of Retinal Neovascularization in vivo by Inhibition of Vascular Endothelial Factor (VEGF) Using Soluable VEGF-Receptor chimeri Proteins," Proc. Natl. Acad. Sci. USA 92:10457-61.
Amano et al., 1998; "Requirement for Vascular Endothelial Growth Factor in Wound-and Inflammation-Related Corneal Neovascularization," Invest Opthaimol Vis Sci. 18-22; Requirement.
Ambati et al.; 1997; "Elevated Gamma-Aminobutyric Acid, Glutamate, and Vascular Endothelial Growth Factor Levels in the Vitreous of Patients with Proliferative Diabetic Retinopathy," Arch Aphtalmol. 115:1161-66.
Ambati et al.; 2002; "Angiostatin Inhibits and Regresses Corneal Neovasculatization," Arch Opthalmol. 120:1063-68.
Amin et al.; 2004; "Inhibiton of VEGF Expression of VEGF Receptor-1 Intrakine," Invest. Opthalmol. Vs. Sci., 45(S2) U526.
Autiero et al., 2003; "Role of PIGF in the Intra-and intermolecular Cross Talk Between the VEGF Receptors Flt1 and Flk1," Nat. Med. 9:936-943.
Carmeliet & Collen, 1999, "Role of vascular Endothelial Growth Factor and Vascular Endothelial Growth Factor in Vascular Development," Top Microbiol. Immunol. 237:133-158.
Casela et al., 2003; "Autocrine-Paracrine VEGF Loops Potentiate the Maturation of Megakaryocytic Precursors throught Flt1 Reception," Blood 101:1316-23.
Chen et al., 1997, "Inactivation of HIV-1 chemokine co-receptor CXCR4 by a novel intrakine strategy." Nat. Med. 3:1110-6.
Cursiefen et al., 2004, "Inhibiton pf Hemangiogenesis and Lymphangiogenesis after Normal-Risk Corneal Transplantation by Neutralizing VEGF Promotes Graft Survival," Invest Opthalmol Vis Sci. 45:2666-73.
Cursiefen et al.; "VEGF-A Stimulates Lymphagiogenesis and Hemangiogensis in Inflammatory Neovascularization via Macrophage Recruitment," J. Clin. Invest. 113:1040-50; 2004.
Dimmeler et al., 2000; "Phosphorylation of the Endothelial Nitric Oxide Synthase at Ser-1177 is Required for VEGF-Induced Endothelial Cell Migration;" FEBS Lett 477:258-62.
Dvorak, 1999; "Vascular Permeability Factor/Vascular Endothelial Growth Factor and the Significance of Microvascular Hyperpermeability in Angiogenesis"; Curr. Top Microbiol. Immuno. 237-97-132.
Epstein et al., 1987; "Corneal Neovascularization"; Cornea 6(4): 250-257.
Folkman, 1990; "Wahat is the Evidence that Tumors are Angiogenesis Dependent?" Journal of the National Cance Institute, 82(1): 4-7.
Fornace et al., 1988; "DNA Damage-Inducible Transcripts in Mamalian Cells"; Proc Natl Acad Sci. USA 85:880-4.

(Continued)

*Primary Examiner* — Quang Nguyen
(74) *Attorney, Agent, or Firm* — Thorpe North & Western LLP

(57) ABSTRACT

The present invention provides an intraceptor that interacts with and decreases activity of with VEGF and/or a VEGFR for the treatment of angiogenesis-related conditions. The present invention further provides pharmaceutical compositions, and methods of use thereof, for the treatment and prevention of an angiogenesis-related condition using said intraceptors. The invention further provides for nucleic acids encoding said intraceptors.

5 Claims, 6 Drawing Sheets

(56) References Cited

OTHER PUBLICATIONS

Gerber et al; 2002; VEGF regulates haematopoietic stem cell survival by an internal autocrine loop mechanism Nature 417;954-58.

Gragoudas et al., 2004; "Pegaptanib for Neovascular Age-Related Macular Degeneration;" N Engl J Med 351;2805-16.

Hasan et al., 2001; "VEGF Antagonists;" Expert Opin. Biol. Ther. 1:703-18.

Honda et al., 2000; "Experimental Subretinal Neovascularization is Inhibited by Adenovirus-Mediated Soluble VEGGflt-1 Receptor Gene Transfection;" Gene Ther. 7:978-75.

Kanno et al., 2000; "roles of Two VEGF Receptors,Flt-1 and KDR, in the Signal Transduction of VEGF Effects in Human Vascular Endothelial Cells;" Oncogene 19:2138-46.

Kaufman, 2002, "Orchestrating the Unfolded Protein Respose in Health and Disease;" J Clin Invest 110:1389-98.

Kendall et al.; 1996; "Identification of a Natural Soluble Form of the Receptor, FLT-1, and its Heterodimerizaion with KDR;" Biochem Biophy Res Comm. 226:324-28.

Kim et al.; 1993; "Inhibition of Vascular Endothelial Growth Factor-Induced Angiogenesis Syppresses Tumour Growth in Vivo;" Nature, 362:841-44.

Ko et al., 2004; "PDI-Mediated ER Retention and Proteasomal Degradation of Procollagen I in Corneal Endothelial Cells"; Exp Cell Res.;295;25-35.

Krietman et al.; "Increased Antitumor Activity of a Circularly Permuted Interleukin 4-Toxin in Mice with Interleukin 4 Receptor-Bearing Human Carcinoma;" Cancer Res. 55:3357-63.

Lee et al.; 1999; "Cell-retained isoforms of vascular endothelial growth factor (VEGF) are correlated with poor prognosis in osteosarcoma;" Eur J Cancer 35:1089-93.

Lin et al. 1998; "Inhibition of Tumor Growth by Targeting Tumor Endothelium Using a Soluble Vascular Endothelial Growth Factor Receptor;" Cell Growth Differ. 9:49-58.

Liu et al., 1998; Regulation of Vascular Endothelial Growth Factor Receptor KDS in vitro by a Soluble Factor in Confluent Endothelial Cells;: Pathobiology 66:247-52.

"Argon Laser Photocoagulation for Neovascular Maculopathy;" Macular Photocoagulation Study Group. Arch Opthalmol. 1991; 109;1109-14.

Masood et al.; 2001; "Human Herpesvirus-8-Transformed Endothelial Cells Have Functionally Activated Vascular Endothelial Growth Factor/Vascular Endothelial Growth Factor Receptor," Blood 98:1904-13.

Millauer et al.; "High Affinity VEGF Binding and Development Expression Suggest Flk-1 as a Major Regulator of Vasculogenesis and Angiogenesis;" (Mar. 1993), Cell, vol. 72, pp. 835-846; Cell Press.

Neufeld et al.; 1999; "Vascular Endothelial Growth Factor (VEGF) and Its Receptors;" FASEB J 13:9-22.

Pelham, 1990; "The Retention Signal for Soluble Proteins of the Endoplasmic Reticulum;" The RTrends Biochem Sci. 15:483-6.

Phillipp et al., 2000; "Expression of Vascular Endothelial Grwoth Factor and its Receptors in Inflamed and Vascularized Human Corneas;" Invent Opthalmol Vis Sci. 41:2514-22.

Pimbs et al.; "Photodynamic Theapy for Corneal Neovascularization;" 1998, 29:832-38.

Robinson et al., 1996; "Oligodeoxynucleotides Inhibit Rential Neovascularization in a Murine model of Proliferative Retinopathy;" Proc. Natl. Acad. Sci. USA 93:4851-56.

Santos et al., 2004; "Internal and externam autocrine VEGF/KDR loops regulate survival of subset of acute leukemia through distinct signaling pathways;" Blood 103:3883-9.

Sato et al.; 2000; "Properties of Two VEGF Receptors, Flt-1 and KDR, in Signal Transductiona;" Ann NY Acad Sci. 902:201-207.

Schroder & Kaufman, 2005; "ER Stress and the Unfolded Protein Response;" Mutat Res. 569:29-63.

Shen et al., 1998; "Homologous Up-regulation of KDR/Flk-1 Receptor Expression by Vascular Endotheliam Growth Factor in Vitro;" J. Biol. Chem, 273:29979-85.

Shen et al., 2002; "Preclinical Evaluatin of a Phosphorothioate Oligonucleotide in the Retina of Rhesus Monkey;" Lab. Invest. 82:167-82.

Singh et al., 2005; "Flt-1 Intraceptors Inhibit Hypoxia-Induced VEGF Expression in Vitro and Corneal Neovascularization in Vivo;" Invest. Opthalmol. Vs. Sci. 46(5):1647-1652.

Steinberg et al., 2000, "Generation and Characterization of a Recombinant Human CCR5-specific Antibody: A phage Display Approach for Rabbit Antibody Humanization;" Proc. Natl. Acad. Sci. 97:805-10.

Straume et al., "Expression of Vascular Endothelial Growth Factor, Its Receptors (FLT-1, KDR), and TSP-1 Related to Microvessel Density and Patient Outcome in Verticakl Growth Phase Melanomas;" Pathol. 159:223-35.

Tang et al.; 1992; "Retention of a Type II Surface Membrane Protein in the Endoplasmic Reticulum by the Lys-Asp-Glu-Leu Sequence;" J. Biol. Chem. 267:7072-6.

Thakker et al., 1999; "The Role of Phosphatidyl 3-Kinase in Veascular Endotheliam Growth Factor Signaling;" J. Biol. Chem. 274:10002-7.

Tirasophon et al. 1998;"A Stress Resonse Pathway from the Endoplasmic Reticulum to the Nucleus Requires a Novel Bifunctional Protein Kinase-Endoribonuclease (Irelp) in Mammalian Cells;" Genes Dev. 12:1812-24.

Wang et al., 1998; "Cloning of Mammalian Ire1 Reveals Diversity in the ER Stress Responses;" EMBO J. 17:5708-17.

Wheeler et al., 2003; "Intrabody-Based Strategies for Inhibition of Vascular Endothelial Growth Factor Receptor-2: Effects on Apoptosis, Cell Growth, and Angiogenesis;" FASEB J. 17:1733-5.

Yamamoto et al.; "The KDEL Receptor Modulates the Endoplasmic Reticulum Stress Response through Mitogen-Activated Protein Kinase Signaling Cascades;" J. Biol. Chem. 278:34525-32.

Yoshida et al., 2001; "XBP1 mRNA is induced by ATF6 and Spliced by IREI in Response to ER Stress to Produce a Highly Active Transcription Factor;" Cell 1079;881-91.

Yuan et al., 1996; "Time Dependent Vascular Regression and Permeability Changes in Established Human Tumor Xenografts Induced by an Anti-Vascular Endothelial Growth Factor/Vascular Permeability Factor Antibody;" Proc. Natl. Acad. Sci. USA 93:14765-70.

Zhang et al.; "AAV2 Delivery of Flt23k Intraceptors Inhibits Murine Choroidal Neovascularization;" Molecular Therapy (Feb. 2015); vol. 23, No. 2; pp. 226-234; The American Society of Gene & Cell Therapy.

* cited by examiner

US 9,447,166 B2

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Lys Asp Glu Leu
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Lys Asp Glu Val
1

<210> SEQ ID NO 3
<211> LENGTH: 648
<212> TYPE: DNA
<213> ORGANISM: Homo sapiens

<400> SEQUENCE: 3
```

```
gatacaggta gacctttcgt agagatgtac agtgaaatcc ccgaaattat acacatgact      60
gaaggaaggg agctcgtcat tccctgccgg gttacgtcac ctaacatcac tgttactttta    120 aaaaagtttc cacttgacac tttgatccct gatggaaaac gcataatctg ggacagtaga    180
aagggcttca tcatatcaaa tgcaacgtac aaagaaatag gcttctgac ctgtgaagca     240 acagtcaatg gcatttgta taagacaaac tatctcacac atcgacaaac caatacaatc     300
atagatgtcc atagatgtcc atagatgtcc atagatgtcc ttagaggcca tactcttgtc     360
ctcaattgta ctgctaccac tcccttgaac acgagagttc aaatgacctg gagttaccct    420
gatgaaaaaa ataagagagc ttccgtaagg cgacgaattg accaaagcaa ttcccatgcc    480
aacatattct acagtgttct tactattgac aaaatgcaga acaaagacaa aggactttat    540
acttgtcgtg taaggagtgg accatcattc aaatctgtta cacctcagt gcatatatat     600 gataaagcat tcatcactgt gaaacatcga aaaaaggacg agctgtaa                  648
```

```
<210> SEQ ID NO 4
<211> LENGTH: 215
<212> TYPE: PRT
<213> ORGANISM: Homo sapiens

<400> SEQUENCE: 4

Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Ala
65                  70                  75                  80

Thr Val Asn Gly His Leu Tyr Lys Thr Asn Tyr Leu Thr His Arg Gln
                85                  90                  95

Thr Asn Thr Ile Ile Asp Val Gln Ile Ser Thr Pro Arg Pro Val Lys
            100                 105                 110

Leu Leu Arg Gly His Thr Leu Val Leu Asn Cys Thr Ala Thr Thr Pro
        115                 120                 125

Leu Asn Thr Arg Val Gln Met Thr Trp Ser Tyr Pro Asp Glu Lys Asn
    130                 135                 140

Lys Arg Ala Ser Val Arg Arg Ile Asp Gln Ser Asn Ser His Ala
145                 150                 155                 160

Asn Ile Phe Tyr Ser Val Leu Thr Ile Asp Lys Met Gln Asn Lys Asp
                165                 170                 175

Lys Gly Leu Tyr Thr Cys Arg Val Arg Ser Gly Pro Ser Phe Lys Ser
            180                 185                 190

Val Asn Thr Ser Val His Ile Tyr Asp Lys Ala Phe Ile Thr Val Lys
        195                 200                 205

His Arg Lys Lys Asp Glu Leu
    210                 215

<210> SEQ ID NO 5
<211> LENGTH: 930
<212> TYPE: DNA
<213> ORGANISM: Homo sapiens
```

<400> SEQUENCE: 5

```
gatacaggta gacctttcgt agagatgtac agtgaaatcc ccgaaattat acacatgact      60
gaaggaaggg agctcgtcat tccctgccgg gttacgtcac ctaacatcac tgttacttta     120
aaaaagtttc cacttgacac tttgatccct gatggaaaac gcataatctg ggacagtaga     180
aagggcttca tcatatcaaa tgcaacgtac aaagaaatag gcttctgac ctgtgaagca      240
acagtcaatg gcatttgta taagacaaac tatctcacac atcgacaaac caatacaatc      300
atagatgtcc aaataagcac accacgccca gtcaaattac ttagaggcca tactcttgtc     360
ctcaattgta ctgctaccac tcccttgaac acgagagttc aaatgacctg gagttaaccc     420
tgatgaaaaa aataagagag cttccgtaag gcgacgaatt gaccaaagca attcccatgc     480
caacatattc tacagtgttc ttactattga caaaatgcag aacaaagaca aggactttta     540
tacttgtcgt gtaaggagtg gaccatcatt caaatctgtt aacacctcag tgcatatata     600
tgataaagca ttcatcactg tgaaacatcg aaaacagcag gtgcttgaaa ccgtagctgg     660
caagcggtct taccggctct ctatgaaagt gaaggcattt ccctcgccgg aagttgtatg     720
gttaaaagat gggttacctg cgactgagaa atctgctcgc tatttgactc gtggctactc     780
gttaattatc aaggacgtaa ctgaagagga tgcaggaat tatacaatct tgctgagcat      840
aaaacagtca atgtgtttta aaacctcac tgccactcta attgtcaatg tgaaacccag      900
atttacgaaa aggccaagga cgagctgtaa                                      930
```

<210> SEQ ID NO 6
<211> LENGTH: 309
<212> TYPE: PRT
<213> ORGANISM: Homo sapiens

<400> SEQUENCE: 6

```
Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
            20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
    50                  55                  60

Ile Ser Asn Ala Thr Tyr Lys Glu Ile Gly Leu Leu Thr Cys Glu Ala
65                  70                  75                  80

Thr Val Asn Gly His Leu Tyr Lys Thr Asn Tyr Leu Thr His Arg Gln
                85                  90                  95

Thr Asn Thr Ile Ile Asp Val Gln Ile Ser Thr Pro Arg Pro Val Lys
            100                 105                 110

Leu Leu Arg Gly His Thr Leu Val Leu Asn Cys Thr Ala Thr Thr Pro
        115                 120                 125

Leu Asn Thr Arg Val Gln Met Thr Trp Ser Tyr Pro Asp Glu Lys Asn
    130                 135                 140

Lys Arg Ala Ser Val Arg Arg Ile Asp Gln Ser Asn Ser His Ala
145                 150                 155                 160

Asn Ile Phe Tyr Ser Val Leu Thr Ile Asp Lys Met Gln Asn Lys Asp
                165                 170                 175

Lys Gly Leu Tyr Thr Cys Arg Val Arg Ser Gly Pro Ser Phe Lys Ser
            180                 185                 190

Val Asn Thr Ser Val His Ile Tyr Asp Lys Ala Phe Ile Thr Val Lys
```

```
                195                 200                 205

His Arg Lys Gln Gln Val Leu Glu Thr Val Ala Gly Lys Arg Ser Tyr
    210                 215                 220

Arg Leu Ser Met Lys Val Lys Ala Phe Pro Ser Pro Glu Val Val Trp
225                 230                 235                 240

Leu Lys Asp Gly Leu Pro Ala Thr Glu Lys Ser Ala Arg Tyr Leu Thr
                245                 250                 255

Arg Gly Tyr Ser Leu Ile Ile Lys Asp Val Thr Glu Glu Asp Ala Gly
            260                 265                 270

Asn Tyr Thr Ile Leu Leu Ser Ile Lys Gln Ser Asn Val Phe Lys Asn
        275                 280                 285

Leu Thr Ala Thr Leu Ile Val Asn Val Lys Pro Gln Ile Tyr Glu Lys
    290                 295                 300

Ala Lys Asp Glu Leu
305

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide

<400> SEQUENCE: 7

Arg Asp Glu Leu
1

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide

<400> SEQUENCE: 8

His Asp Glu Leu
1

<210> SEQ ID NO 9
<211> LENGTH: 35
<212> TYPE: DNA
<213> ORGANISM: Artificial Sequence
<220> FEATURE:
<223> OTHER INFORMATION: Synthetic primer

<400> SEQUENCE: 9
taggatccat ggatacaggt agacctttcg tagag                          35

<210> SEQ ID NO 10
<211> LENGTH: 45
<212> TYPE: DNA
<213> ORGANISM: Artificial Sequence
<220> FEATURE:
<223> OTHER INFORMATION: Synthetic primer

<400> SEQUENCE: 10
tagaattcta ttacagctcg tccttttttc gatgtttcac agtga               45

<210> SEQ ID NO 11
<211> LENGTH: 44
<212> TYPE: DNA
<213> ORGANISM: Artificial Sequence
<220> FEATURE:
```

<223> OTHER INFORMATION: Synthetic primer

<400> SEQUENCE: 11
tagaattcta ttacagctgg tccttggcct tttcgtaaat ctgg                    44

<210> SEQ ID NO 12
<211> LENGTH: 4017
<212> TYPE: DNA
<213> ORGANISM: Homo sapiens

<400> SEQUENCE: 12

| | |
|---|---|
| atggtcagct actgggacac cggggtcctg ctgtgcgcgc tgctcagctg tctgcttctc | 60 |
| acaggatcta gttcaggttc aaaattaaaa gatcctgaac tgagtttaaa aggcacccag | 120 |
| cacatcatgc aagcaggcca gacactgcat ctccaatgca ggggggaagc agcccataaa | 180 |
| tggtctttgc ctgaaatggt gagtaaggaa agcgaaaggc tgagcataac taaatctgcc | 240 |
| tgtggaagaa atggcaaaca attctgcagt actttaacct tgaacacagc tcaagcaaac | 300 |
| cacactggct tctacagctg caaatatcta gctgtaccta cttcaaagaa gaaggaaaca | 360 |
| gaatctgcaa tctatatatt tattagtgat acaggtagac cttttcgtaga gatgtacagt | 420 |
| gaaatccccg aaattataca catgactgaa ggaagggagc tcgtcattcc ctgccggtt | 480 |
| acgtcaccta acatcactgt tactttaaaa agtttccac ttgacacttt gatccctgat | 540 |
| ggaaaacgca taatctggga cagtagaaag ggcttcatca tatcaaatgc aacgtacaaa | 600 |
| gaaataggcc ttctgacctg tgaagcaaca gtcaatgggc atttgtataa gacaaactat | 660 |
| ctcacacatc gacaaaccaa tacaatcata gatgtccaaa taagcacacc acgcccagtc | 720 |
| aaattactta gaggccatac tcttgtcctc aattgtactg ctaccactcc cttgaacacg | 780 |
| agagttcaaa tgacctggag ttaccctgat gaaaaaaata gagagcttc cgtaaggcga | 840 |
| cgaattgacc aaagcaattc ccatgccaac atattctaca gtgttcttac tattgacaaa | 900 |
| atgcagaaca agacaaagg actttatact tgtcgtgtaa ggagtggacc atcattcaaa | 960 |
| tctgttaaca cctcagtgca tatatatgat aaagcattca tcactgtgaa acatcgaaaa | 1020 |
| cagcaggtgc ttgaaaccgt agctggcaag cggtcttacc ggctctctat gaaagtgaag | 1080 |
| gcatttcct cgccggaagt tgtatggtta aaagatgggt acctgcgac tgagaaatct | 1140 |
| gctcgctatt tgactcgtgg ctactcgtta attatcaagg acgtaactga agaggatgca | 1200 |
| gggaattata caatcttgct gagcataaaa cagtcaaatg tgtttaaaaa cctcactgcc | 1260 |
| actctaattg tcaatgtgaa accccagatt acgaaaagg ccgtgtcatc gtttccagac | 1320 |
| ccggctctct acccactggg cagcagacaa atcctgactt gtaccgcata tggtatccct | 1380 |
| caacctacaa tcaagtggtt ctggcacccc tgtaaccata atcattccga agcaaggtgt | 1440 |
| gacttttgtt ccaataatga gagtcctct atcctggatg ctgacagcaa catgggaaac | 1500 |
| agaattgaga gcatcactca gcgcatggca ataatagaag gaagaataa gatggctagc | 1560 |
| accttggttg tggctgactc tagaatttct ggaatctaca tttgcatagc ttccaataaa | 1620 |
| gttgggactg tgggaagaaa cataagcttt tatatcacag atgtgccaaa tgggtttcat | 1680 |
| gttaacttgg aaaaaatgcc gacggaagga gaggacctga actgtcttg cacagttaac | 1740 |
| aagttcttat acagagacgt tacttggatt ttactgcgga cagttaataa cagaacaatg | 1800 |
| cactacagta ttagcaagca aaaaatggcc atcactaagg agcactccat cactcttaat | 1860 |
| cttaccatca tgaatgtttc cctgcaagat tcaggcacct atgcctgcag agccaggaat | 1920 |
| gtatacacag gggaagaaat cctccagaag aaagaaatta caatcagaga tcaggaagca | 1980 |

-continued

```
ccatacctcc tgcgaaacct cagtgatcac acagtggcca tcagcagttc caccacttta    2040
gactgtcatg ctaatggtgt ccccgagcct cagatcactt ggtttaaaaa caaccacaaa    2100
atacaacaag agcctggaat tattttagga ccaggaagca gcacgctgtt tattgaaaga    2160
gtcacagaag aggatgaagg tgtctatcac tgcaaagcca ccaaccagaa gggctctgtg    2220
gaaagttcag catacctcac tgttcaagga acctcggaca agtctaatct ggagctgatc    2280
actctaacat gcacctgtgt ggctgcgact ctcttctggc tcctattaac cctctttatc    2340
cgaaaaatga aaggtcttc ttctgaaata aagactgact acctatcaat tataatggac    2400
ccagatgaag ttcctttgga tgagcagtgt gagcggctcc cttatgatgc cagcaagtgg    2460
gagtttgccc gggagagact taaactgggc aaatcacttg aagaggggc ttttggaaaa    2520 gtggttcaag catcagcatt tggcattaag aaatcaccta cgtgccggac tgtggctgtg    2580
aaaatgctga agagggggc cacggccagc gagtacaaag ctctgatgac tgagctaaaa    2640
atcttgaccc acattggcca ccatctgaac gtggttaacc tgctgggagc ctgcaccaag    2700
caaggagggc ctctgatggt gattgttgaa tactgcaaat atggaaatct ctccaactac    2760
ctcaagagca aacgtgactt atttttttctc aacaaggatg cagcactaca catggagcct    2820
aagaaagaaa aaatggagcc aggcctggaa caaggcaaga accaagact agatagcgtc    2880 accagcagcg aaagctttgc gagctccggc tttcaggaag ataaaagtct gagtgatgtt    2940
gaggaagagg aggattctga cggtttctac aaggagccca tcactatgga agatctgatt    3000
tcttacagtt ttcaagtggc cagaggcatg gagttcctgt cttccagaaa gtgcattcat    3060
cgggacctgg cagcgagaaa cattctttta tctgagaaca acgtggtgaa gatttgtgat    3120
tttggccttg cccgggatat ttataagaac cccgattatg tgagaaaagg agatactcga    3180
cttcctctga atggatggc tcctgaatct atctttgaca aaatctacag caccaagagc    3240
gacgtgtggt cttacggagt attgctgtgg gaaatcttct ccttaggtgg gtctccatac    3300
ccaggagtac aaatggatga ggacttttgc agtcgcctga gggaaggcat gaggatgaga    3360
gctcctgagt actctactcc tgaaatctat cagatcatgc tggactgctg gcacagagac    3420
ccaaaagaaa ggccaagatt tgcagaactt gtggaaaaac taggtgattt gcttcaagca    3480
aatgtacaac aggatggtaa agactacatc caatcaatg ccatactgac aggaaatagt    3540
gggtttacat actcaactcc tgccttctct gaggacttct tcaaggaaag tatttcagct    3600
ccgaagttta attcaggaag ctctgatgat gtcagatatg taaatgcttt caagttcatg    3660
agcctggaaa gaatcaaaac ctttgaagaa cttttaccga atgccacctc catgtttgat    3720
gactaccagg gcgacagcag cactctgttg gcctctccca tgctgaagcg cttcacctgg    3780
actgacagca aacccaaggc ctcgctcaag attgacttga gagtaaccag taaaagtaag    3840
gagtcggggc tgtctgatgt cagcaggccc agtttctgcc attccagctg tgggcacgtc    3900
agcgaaggca gcgcaggtt cacctacgac cacgctgagc tggaaaggaa aatcgcgtgc    3960 tgctcccgc ccccagacta caactcggtg gtcctgtact ccaccccacc catctag      4017
```

<210> SEQ ID NO 13
<211> LENGTH: 480
<212> TYPE: PRT
<213> ORGANISM: Homo sapiens

<400> SEQUENCE: 13

Met Val Ser Tyr Trp Asp Thr Gly Val Leu Leu Cys Ala Leu Leu Ser
1               5                   10                  15

```
Cys Leu Leu Leu Thr Gly Ser Ser Gly Ser Lys Leu Lys Asp Pro
             20              25              30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
 50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430
```

```
Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480
```

COMPOSITIONS AND METHODS FOR THE INTRACELLULAR DISRUPTION OF VEGF AND VEGFR-2 BY INTRACEPTORS

CROSS REFERENCE TO RELATED APPLICATIONS

This application is a continuation of U.S. patent application Ser. No. 13/540,495, filed Jul. 2, 2012, which is a continuation of U.S. patent application Ser. No. 11/814,890, filed Oct. 22, 2007, now issued as U.S. Pat. No. 8,211,864, which is a U.S. national stage entry of PCT Application Ser. No. PCT/US2006/002684, filed Jan. 26, 2006, which claims the priority benefit of U.S. Provisional Patent Application Ser. No. 60/647,224, filed Jan. 26, 2005, each of which is incorporated herein by reference.

BACKGROUND OF THE INVENTION

1. Field of the Invention

This invention relates generally to compositions and methods for inhibiting angiogenesis. In particular, this invention relates to compositions comprising intraceptors, and methods of use thereof, to disrupt the intracellular expression and/or secretion of a vascular endothelial growth factors (VEGF) and/or vascular endothelial growth factor receptor (VEGFR). In certain embodiments, such itraceptors can be used to treat angiogenesis related condition.

BACKGROUND ART

Angiogenesis, the growth of new blood vessels, is a fundamental biological process which plays a central role in the pathogenesis of various conditions, and is a major contributor to mortality and morbidity in diseases, such as cancer, diabetic retinopathy, and macular degeneration (Folkman, 1990, JNCI 82; 4-6). Cancer is the second loading cause of death in the United States, claiming 553,251 lives in 2001 (National Vital Statistics Report. 2003). Diabetic retinopathy affects over 53 million Americans, and is the leading cause of new blindness among U.S. adults 20-74 years of age. Proliferative diabetic retinopathy (PDR) is a condition in which, abnormal new blood vessels in the retina may rupture and bleed inside the eye, and is a principal cause of blindness in diabetics. The prevalence of PDR increases from 2% at diagnosis to 20% after 20 years of disease (Morbidity and Mortality Weekly Report, 1993, pp. 191-95). The estimated incidence of new PDR cases is about 65,000 per year. Age-related macular degeneration (AMD) is the leading cause of irreversible blindness among those over 65 in the United States, Western Europe, and Japan and affects over 11 million persons in the US. More than 20% of the American population is older than 55 years of age and at risk for AMD. Each year, more than a million individuals softer severe central vision loss due to AMD; these numbers will, skyrocket with the aging population. Neovascular AMD is responsible for severe vision loss in 80-90% of these patients (Macular Photocoagulation Study Group. Arch Ophthalmol. 1991; 109:1109-14).

Corneal neovascularization is a central feature in the pathogenesis of many blinding corneal disorders, and a major sight-threatening complication in corneal infections, chemical injury, and following, keratoplasty, in which neovascularization adversely impacts corneal transplant survival (Epstein et al., 1987, Cornea. 6:250-57). Anti-angiogenic molecules have been shown to inhibit corneal neovascularization (Ambati et al., 2002, Arch Ophthalmol 120; 1063-68). Thermal laser and photodynamic therapy induces only temporary closure of new vessels (Primbs et al., 1998,29; 832-38), without addressing the underlying biology of neovascularization.

Annually, approximately 45,000 corneal transplants are performed in the US. This is the highest number for any transplant, largely because of high success conferred by the immune privilege of the normally avascular cornea. Corneal neovascularization breaches this immune privilege, and is a major factor in rejection of corneal transplants, which occurs in about 10% of cases.

Vascular endothelial, growth factor (VEGF) is a key mediator of angiogenesis in many models (Nenfeld et al., 1999, FASEB J. 13; 9; Dvorak, 1999, Curr. Top Microbiol. Immunol. 237: 97; and Carmeliet & Collen, 1999, Curr. Top Microbiol. Immunol. 237: 133, etc.). VEGF promotes vascular endothelial cell migration, proliferation, inhibition of apoptosis, vasodilation, and increased vascular permeability. In several clinically relevant models of animal and human corneal neovascularization, angiogenesis is driven by increased secretion of VEGF-A (herein referred to as VEGF) (Amano et al., 1998, Invest Ophthalmol Vis Sci. 18-22; Cursiefen et al., 2004, J. Clin Invest. 113: 1040-50; and Philipp et al., 2000, Invest Ophthalmol Vis Sci. 41: 2514-22), and is also closely linked to infiltrating leukocytes (Amano et al., 1998, Invest Ophthalmol Vis Sci. 18-22).

Three receptors constitute the VEGF receptor family, which includes VEGFR-1 (Flt or Flt-1), VEGFR-2 (KDR), and VEGFR-3 (Flt-4), all of which have tyrosine-kinase activity (Neufeld et al., 1999, FASEB J. 13.9). The cDNA and amino acid sequences of human Flt-1 are found at accession number gi:56385329. Several studies have shown VEGFR-2 (through activation of MAP kinase and P1-3K (phosphatidylinositol 3-kinase) is the signal transducer tot VEGF-induced mitogenesis, chemotaxis, and cytoskeletal reorganization and thus the principal receptor involved in angiogenesis (Thakker et al., 1999 J. Biol. Chem. 274; 10002-7; Dimmeler et al., 2000, FEBS Lett 477:258-62; Carmeliet & Collen, 1999, Curr. Top Microbol. Immunol. 237:97; Neufeld et al., 1999% FASEB J. 13:9; and Millauer et al., 1993, Cell 72: 835-46). VEGFR-3 is primarily involved in lymphangiogenesis (Cursiefen et al., 2004, Invest Ophthalmol Vis Sci. 45; 2666-73; Cursiefen et al., 2004, J. Clin Invest 113: 1040-50).

VEGF transcription is amplified in response to oncogenes, hypoxia, and other insults. Transcription factors for VEGF (HIF-$1\alpha$ and HIF-$2\alpha$) are stabilised during hypoxia (Ahmed et al., 2000, Placenta 21 SA:S16-24; Wenger & Gassman, 1997, Biol. Chem. 378:609). Sensitivity to hypoxia is a major difference between VEGF and other angiogenic factors (Arbiser et al., 1997, Proc. Natl. Acad. Sci USA 94: 861; Okada et al., 1998, Proc., Natl, Acad, Sci. USA 95: 3609; and Petit at al, 1997, Am. J, Pathol. 151: 1523). Elevated VEGF has been associated with a poor prognosis in cancer and with diabetic retinopathy (Ambati et al., 1997, Arch Ophthalmol 115: 1161-66). Strategies to inhibit VEGF have included blocking antibodies, decoy receptors for VEGF, and anti-VEGF antibodies (Kim et al., 1993, Nature 362; 841-44; Yuan, et al., 1996, Proc. Natl. Acad, Sci, USA. 93:14765-70; Lin et al, 1998, Cell Growth Differ. 9: 49-58; and Hasan & Jayson, 2001, Expert Opin Biol Ther. 1: 703-18). These strategies have generally reduced neovascularization by only 30-50% (Robinson et al., 1996, Proc. Natl Acad Sci USA 93; 4851-56; Aiello et al. 1995, Free, Natl. Acad. Sci USA 92: 10457-61; Shen et al., 2002, Lab Invest 82:167-82; and Honda et al., 2000, Gene Ther. 7:978-75). These levels of neovascularization reduction are insufficient for the cornea, where angiogenesis should be minimized as much as possible for optimal visual clarity.

Further, in the course of normal VEGF signal transduction, membrane Flt heterodimerizes with VEGFR-2 upon VEGF binding (Autiero et al., 2003, Nat. Med.; and Kendall et al., 1996, Biochem Biophy Res Comm. 226:324-28). Physiologic Flt/VEGFR-2 heterodimers stimulate expression of fee genes for the transcription factor Ets-1 and matrix metalloproteinase 1 (MMP-1), phosphorylation of focal adhesive kinase (FAK), vinculin assembly and DNA synthesis (Kanno et al., 2000, Oncogene 19: 2138-46; Sato et al., 2000, Ann NY Acad Sci. 902:201-7). Ets-1 induces expression of Beatrix metalloproteinase 1 (MMP-1), MMP-3, MMP-9, matrix plasminogen activator; and β3 integrin b, all involved, in matrix-neovessel interactions. MMP-1 facilitates digestion, of extracellular matrix to facilitate vascular ingrowth, while FAK helps mediate adhesion among endothelial cells and extracellular matrix. These events are critical to endothelial cell migration and proliferation.

KDEL (SEQ ID NO: 1) is the one letter sequence for the peptide retention signal having the amino mid sequence Lys-Asp-Glu-Leu (SEQ ID NO: 1) which, binds endoplasmic reticulum retention receptors, thus preventing secretion of ligands of proteins coupled to the sequence (Pelham, 1990, Trends Biochem Sci. 15:483-6). This is also a highly specific retention sequence, as constructs using a KDEV (SEQ ID NO:2) sequence are not successful at retaining targets (Tang et al. 1992, J. Biol Chem. 267:7072-6), Although the mechanism of clearance or degradation of KDEL-sequestered (SEQ ID NO:1) proteins is not fully known, the ubiquitin-proteasome pathway is thought to be the principal route for clearance of intraceptor-retained proteins, as removal of KDEL (SEQ ID NO:1) from PDI, an ER chaperone has recently been described to release its target protein, procollagen 1, from ubiquitin-proteasome degradation (ko & Kay, 2004, Exp Cell Res. 295: 25-35).

Linkage of KDEL (SEQ ID NO:1) to chemokines (known as creation of "intrakines") downregulates cognate receptors with significant roles in disease (Chen et al., 1997, Nat. Med. 3: 1110-6; Kreitean et al., 1995, Cancer Res. 55: 3357-63). Coupling stromal derived factor (SDF) wife KDEL (SEQ ID NO: 1) blocked cell surface expression of SDF's receptor, CXCR-4; similar efforts have been used to downregulate cell surface expression of other receptors, including CCR-5 and Interleukin-4 receptor (Kreitman et al., 1995, Cancer Res. 55: 3357-63; Luis et al., 2003, Mol Ther. 8: 475-84; and Steinberger et al., 2000, Proc Natl Acad. Sci. 97: 805-10).

It has been, reported that sequestered proteins are eventually degraded in the endoplasmic reticulum (Pelham, 1990, Trends Biochem Sci. 15: 483-6). The accumulation of sequestered, proteins in the endoplasmic reticulum may lead to endoplasmic reticulum overload, triggering the unfolded protein response (UPR), which could cause apoptosis of endothelial cells, as the presence of unfolded proteins in endoplasmic reticulum (ER) leads to a stress response including release of pro-apoptotic factors such as CHOP and caspase-12 (Wang et al., 1998, EMBO J. 17: 5708-17; Yoshida et al., 2001, Cell 107: 881-91; Tirasophon et al., 1998, Genes Dev. 12:812-24; Fornace et al., 1988, Proc Natl Acad Sci USA 85: 8800-4; Kaufman, 2002, J Clin Invest 110: 1389-98; and Schroder & Kaufman, 2005, Mutat Res. 569; 29-63). Although the effect of KDEL (SEQ ID NO:1)-mediated protein retention on these molecular responses is unknown, it has been reported that the KDEL (SEQ ID NO:1) receptor is involved in the ER stress response (Yamamoto et al. 2003, J. Biol Chem. 278: 34525-32).

VEGF is an important target for inhibiting angiogenesis. Molecular interventions such as anti-VEGF aptamers or antibodies (e.g. Macugen; Eyetech) and ranibizumab (Lucentis; Genentech) are currently used or under investigation for AMD and PDR, but are based on extracellular blockade of VEGF. Intracellular approaches against VEGF could potentially ameliorate these conditions, as results for extracellular modalities have been mixed (Gragoudas et al., 2004, N Engl J Med 351; 2805-16), or add a new additional means to affectively reduce total VEGF function.

It is important to target VEDF intracellularly, as several cell types respond to their own VEGF production in an autocrine fashion. VEGF autocrine loops have also been demonstrated in endothelial cells (Honda et al, .2000, Gene Ther. 7: 978-75; Lee et al, 1999, Eur J Cancer 35: 1089-93), including in hypoxic HUVEC cells (Lee et al, 1999, Eur J Cancer 35: 1089-93; Liu & Ellis, 1998, Pathobiology 66; 247-52); further, VEGF can upregulate its own receptor VEGFR-2 (Shen et al., 1998, J. Biol Chem. 273: 29979-85). Cancer cells producing VEGF and VEGFR-2 include prostate carcinoma, leukemia, pancreatic carcinoma, melanoma, Kaposi's sarcoma, and osteosarcoma (Lee et al. 1999, Eur J Cancer 35: 1089-93; Masood et al., 2001, Blood 98: 1904-13). Intracellular autocrine loops render cells resistant to modalities targeting VEGF extracellularly (Gerber et al., 2002, Nature 417: 954-58; Santos & Dias, 2004, Blood 103: 3883-9).

Intracellularly disrupting VEGF expression is potentially superior to extracellular blockade by antibodies or aptamers as intracellular gene silencing may sabotage intracellular autocrine loops that have been demonstrated for VEGF in cancer and endothelial cells (Lee et al., 1999, Eur J Cancer. 35: 1089-93; Liu & Ellis, 1998, Pathobiology 66: 247-52; Casella et al., 2003, Blood 101: 3316-23; Gerber et al. 2002, Nature 417; 954-58; Straume & Akslen, 2001, Pathol. 159: 223-35). Intracellular disruption, of VEGF signaling may represent a powerful addition to the anti-angiogenic arsenal, by sabotaging VEGF secretion and intracellular autocrine loops.

Alternative gene silencing approaches allying on RNAi, antisense oligonucleotides or ribozymes for disrupting VEGF expression, and approaches to sequester VEGF using PIGF-KDEL (SEQ ID NO:1) are previously described in the art. However, since placental growth factor (PIGF) can heterodimerize with VEGF or a complex of an anti-VEGF Fab fragment with KDEL (SEQ ID NO:1; Wheeler et al., 2003, FASEB J 17: 1733-5), there is a need to develop a more effective approach for disrupting both VEGF and VEGFR-2 intracellularly for treating or preventing angiogenesis. Such approach can induce the unfolded protein response in cells that produce VEGF, resulting in selective ER stress. Furthermore, such approach is able to disrupt physiologic heterodimer formation of Flt/VEGFR-2, providing high specificity and affinity for the target molecule due to the use of a receptor as the therapeutic substance.

SUMMARY OF THE INVENTION

The present invention provides for an intraceptor comprising a polypeptide encoded by a nucleotide sequence encoding at least a portion of an extracellular receptor, operatively linked to a signal retention peptide. In certain embodiments, the intraceptor interacts with a ligand for said extracellular receptor, and interaction decreases activity of the extracellular receptor. The invention also encompasses an isolated nucleic acid encoding at least a portion of an extracellular receptor, operatively linked to a nucleic acid encoding a signal retention polypeptide.

In specific embodiments, the invention contemplates an isolated nucleic acid comprising a mil-length polynucleotide selected from the group consisting of (a) a polynucleotide as defined in SEQ ID NO:3; (b) a polynucleotide as defined in SEQ ID NO:S; (c) a polynucleotide encoding a polypeptide as defined in SEQ ID NO:4; (d) a polynucleotide encoding a polypeptide as defined in SEQ ID NO: 6; and (e) a polynucleotide complementary to a full-length polynucleotide of any one of a) through d) above. Also contemplated are an isolated nucleic acid comprising a full-length polynucleotide encoding a polypeptide having at least 80% sequence identity with a polypeptide as defined in SEQ ID NO:4 or SEQ ID NO:6, and wherein said polypeptide Interacts with VEGF and/or VEGFR-2, and an isolated nucleic acid comprising a polynucleotide that hybridizes under highly stringent conditions to a second nucleic acid selected from the group consisting of (a) a polynucleotide as defined in SEQ ID NO:3 or SEQ ID NO:5; and (b) a polynucleotide encoding a polypeptide as defined in SEQ ID NO: 4 or SEQ ID NO:6, wherein said nucleic acid encodes a polypeptide that interacts with VEGF and/or VEGFR-2, and wherein the stringent conditions comprise hybridization in a 6X SSC solution at 65° C. It is contemplated that the interaction of the encoded polypeptide with VEGF and/or VEGFR-2 will decrease the activity of VEGF and/or VEGFR-2.

The invention also encompasses specific intraceptors, such as an intraceptor that interacts with VEGF and/or a VEGFR, comprising a chimeric polypeptide comprising a portion of SEQ ID NO: 13 operatively linked to a signal retention peptide or a polypeptide having at least 80% sequence identity with 30 consecutive amino acids of SEQ ID NO: 13 operatively linked to a signal retention peptide. In certain embodiments, the portion, of SEQ ID NO: 13 comprises amino acids 1-305 of SEQ ID NO:6; or comprises amino acids 1-211 of SEQ ID NO:4. In other embodiments, the intraceptor is selected from the group consisting of (a) a polypeptide as defined in SEQ ID NO:4; (b) a polypeptide as defined in SEQ ID NO: 6; and (c) a polypeptide having at least 80% sequence identity with the polypeptide of a) through b) above. In other embodiments, the chimeric polypeptide comprises a polypeptide having at least 81%, 82%, 83%, 84%, 85%, 86%, 87%, 88%, 89%, 90%, 91%, 92%, 93%, 94%, 95%, 96%, 97%, 98%, 99% or more sequence Identity with at least 30, 40, 50, 60, 70, 80, 90, 100 or more consecutive amino acids of SEQ ID NO: 13 operatively linked to a signal retention peptide.

It is contemplated that the VEGFR can be selected from the group consisting of VEGFR-1, VEGFR-2 and VEGFR-3. In one embodiment, the VEGFR is VEGFR-2.

In certain embodiments, said signal retention peptide can prevent secretion of a peptide operatively linked to the signal retention peptide. In one embodiment, the signal retention peptide is an endoplasmic reticulum signal retention peptide selected from the group consisting of SEQ ID NOs:1, 7, or 8. In particular embodiments, the endoplasmic reticulum signal retention peptide is SEQ ID NO:1.

The invention also contemplates a pharmaceutical composition for treating an angiogenesis-related condition comprising an intraceptor. Also encompassed within the invention are methods of heating an angiogenesis-related condition using the intraceptors and pharmaceutical compositions described herein to contact a cell involved in the angiogenesis-related condition. Preferably, the angiogenesis-related condition is selected from the group consisting of inflammation, stroke, hemangioma, solid tumors, leukemias, lymphomas, myelomas, metastasis, telangiectasia psoriasis scleroderma, pyogenic granuloma, myocardial angiogenesis, plaque neovascularization, coronary collaterals, ischemic limb angiogenesis, corneal diseases, robeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, placentation, polycystic ovary syndrome, dysfunctional uterine bleeding, endometrial hyperplasia and carcinoma, endometriosis, failed implantation and subnormal foetal grow, myometrial fibroids (uterine leiomyomas) and adenomyosis, ovarian hyperstimulation syndrome, ovarian carcinoma, melanoma, venous ulcers, acne, rosacea, warts, eczema, neurofibromatosis, tuberous sclerosis, and chronic inflammatory disease. More preferably, the angiogenesis-related condition is selected from the group consisting of melanoma, diabetic retinopathy, and macular degeneration.

The invention further encompasses a method of inhibiting angiogenesis in a biological sample, comprising (a) providing a biological sample; and (b) combining the sample with a angiogenesis-inhibiting amount of an intraceptor that decreases activity of VEGF and/or a VEGF-R, wherein comprises a chimeric polypeptide comprising a portion of SEQ ID NO: 13 operatively linked to a signal retention peptide, or a polypeptide having at least 80% sequence identity with 30 consecutive amino acids of SEQ ID NO: 13 operatively linked to a signal retention peptide, wherein said contact decreases activity of VEGF and/or a VEGFR. It is contemplated that the biological sample can from a mammal, or specifically, can be a human biological sample. It is farther contemplated that the biological sample can be in a patient and the patient have an angiogenesis-related condition.

BRIEF DESCRIPTION OF THE DRAWINGS

FIG. 4A shows mouse corneas injected with saline, empty pCMV, pCMV.Flt23K, and pCMV.Flt24K, respectively, 1 week post corneal injury. Diffuse neovascularization is present in control, while neovascularization is inhibited where intraceptors were injected. FIG. 4B illustrates that both intraceptors suppress corneal VEGF concentration 2 days after injury. FIG. 4C illustrates that delivery of pCMV.Flt23K or pCMV.Flt24K significantly suppress corneal leukocyte infiltration 1 week after injury relative to Sham saline/PBS or empty pCMV control.

FIG. 10 illustrates RT-PCT results for CHOP that was performed 24 hours after transfection of HMEC. The CHOP mRNA transcript as measured by semiquantitative densitometry was elevated 60% by Flt23K and 80% by Flt24K over the levels in cells transfected with the control plasmid. Lane 1; HMEC cells in media; 2: transfected with empty pCMV; 3: transfected with pCMV.Flt23K; 4: transfected with pCMV.Flt24K.

DETAILED DESCRIPTION OF THE INVENTION

Figure 1:
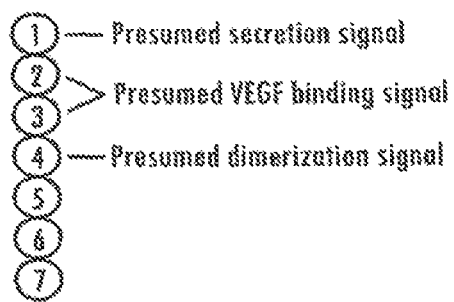
FIG. 1 represents VEGFR-1 (FLT). It consists of 7 domains, and has the highest affinity to VEGF, with a ten-fold higher binding affinity than VEGFR-2. It is a tyrosine kinase receptor with seven Ig-like extracellular domains and a tyrosine kinase domain with a long kinase insert. Domain deletion studies have shown that a subunit construct of domains 2-3 binds VEGF with near wild-type affinity and that domain 1 serves as a secretion signal sequence. Further, domain 4 is necessary for receptor homodimerization of FLT and is believed to be necessary for the observed heterodimerization of FLT and VEGFR-2.

The present invention may be understood more readily by reference to the following detailed description of the preferred embodiments of the invention and the Examples included herein. However, before the present compounds, compositions, and methods ate disclosed and described, it is to be understood that this invention is not limited to specific nucleic acids, specific polypeptides, specific cell types, specific host cells, specific conditions, or specific methods, etc., as such may, of course, vary, and the numerous modifications and variations therein mil be apparent to those skilled in the art. It is also to be understood, that the terminology used herein is for fee purpose of describing specific embodiments only and is not intended to be limiting. It is further to be understood that unless specifically defined herein, the terminology used herein is to be given its traditional meaning as known in the relative art.

The present invention provides for an intraceptor comprising a polypeptide encoded by a nucleotide sequence encoding at least a portion of an extracellular receptor, operatively linked to a signal retention peptide. In certain embodiments, the intraceptor interacts with a ligand tor said extracellular receptor, and interaction decreases activity of the extracellular receptor. The invention also encompasses an isolated nucleic acid encoding at least a portion of an extracellular receptor, operatively linked to a nucleic, acid encoding a signal retention polypeptide.

In specific embodiments, the invention contemplates an isolated nucleic acid, comprising a full-length polynucleotide selected from the group consisting of (a) a polynucleotide as defined in SEQ ID NO:3; (b) a polynucleotide as defined in SEQ ID NO:5; (c) a polynucleotide encoding a polypeptide as defined in SEQ ID NO:4; (d) a polynucleotide encoding a polypeptide as defined in SEQ ID NO:6; and (e) a polynucleotide complementary to a full-length polynucleotide of any one of a) through d) above. Also contemplated are an isolated nucleic acid comprising a full-length polynucleotide encoding a polypeptide having at least 80% sequence identity with a polypeptide as defined in SEQ ID NO:4 or SEQ ID NO:6, and wherein said polypeptide interacts with VEGF and/or VEGFR-2, and an isolated nucleic acid comprising a polynucleotide that hybridizes under highly stringent conditions to a second nucleic acid selected from the group consisting of (a) a polynucleotide as defined in SEQ ID NO: 3 or SEQ ID NO:5; and (b) a polynucleotide encoding a polypeptide as defined in SEQ ID NO:4 or SEQ ID NO;6, wherein said nucleic acid encodes a polypeptide that interacts with VEGF and/or VEGFR-2, and wherein the stringent conditions comprise hybridation in a 6X SSC solution at 65° C. It is contemplated that the interaction, of the encoded polypeptide with VEGF and/or VEGFR-2 will decrease the- activity of VEGF and/or VEGFR-2.

The invention also encompasses specific intraceptors, such as an intraceptor that interacts with. VEGF and/or a VEGFR, comprising a chimeric polypeptide comprising a portion of SEQ ID NO:13 operatively linked to a signal retention peptide or a polypeptide having at least 80% sequence identity with 30consecutive amino acids of SEQ ID NO:13 operatively linked to a signal retention peptide. In certain embodiments, the portion of SEQ ID NO: 13 comprises amino acids 1-305 of SEQ ID NO:6; or comprises amino acids 1-211 of SEQ ID NO:4. In other embodiments, the intraceptor is selected from, the group consisting of (a) a polypeptide as defined In SEQ ID NO:4; (b) a polypeptide as defined in SEQ ID NO:6; and (c) a polypeptide having at least 80% sequence identity with the polypeptide of a) through b) above. In other embodiments, the chimeric polypeptide comprises a polypeptide having at least 81%, 82%, 83%, 84%, 85%, 86%, 87%, 88%, 89%, 90%, 91%, 92%, 93%, 94%, 93%, 96%, 97%, 9.8%, 99% or more sequence identity with at least 30, 40, 50, 60, 70, 80, 90, 100 or more consecutive amino acids of SEQ ID NO:13 operatively linked to a signal retention peptide.

It is contemplated that the VEGFR can he selected from the group consisting of VEGFR-1, VEGFR-2 and VEGFR-3. In one embodiment, the VEGFR is VEGFR-2.

In certain embodiments, said signal retention peptide can prevent secretion of a peptide operatively linked to the signal retention peptide. In one embodiment the signal retention peptide is an endoplasmic reticulum signal retention peptide selected from the group consisting of SEQ ID NOs: 1, 7 or 8. In particular embodiments, the endoplasmic reticulum signal retention peptide is SEQ ID NO:1

The invention also contemplates a pharmaceutical composition for treating an angiogenesis-related condition comprising an intraceptor. Also encompassed within the invention are methods of treating an angiogenesis-related condition using the intraceptors and pharmaceutical compositions described herein to contact a cell involved in the angiogenesis-related condition. Preferably, the angiogenesis-related condition is selected from fee group consisting of inflammation, stroke, hemangioma, solid tumors, leukemias, lymphomas, myelomas, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis ovulation, menstruation, placentation, polycystic ovary syndrome, dysfunctional uterine bleeding, endometrial hyperplasia and carcinoma, endometriosis, failed implantation and subnormal foetal growth, myometrial fibroids (uterine leiomyomas) and adenomyosis, ovarian hyperstimulation syndrome, ovarian carcinoma, melanoma, venous ulcers, acne, rosacea, warts, eczema, neurofibromatosis, tuberous sclerosis, and chronic infammatory disease. More preferably, the angiogenesis-related condition is selected from the group consisting of melanoma, diabetic retinopathy, and macular degeneration.

The invention farmer encompasses a method of inhibiting angiogenesis in a biological sample, comprising (a) providing a biological sample; and (b) combining the sample with a angiogenesis-inhibiting amount of an intraceptor that decreases activity of VEGF and/or a VEGF-R, wherein comprises a chimeric polypeptide comprising a portion of SEQ ID NO:13 operatively linked to a signal retention peptide, or a polypeptide having at least 80% sequence identity with 30 consecutive amino acids of SEQ ID NO:13 operatively linked to a signal retention peptide, wherein said contact decreases activity of VEGF and/or a VEGFR. It is contemplated that the biological sample can from a mammal, or specifically, can be a human biological sample. It is further contemplated that the biological sample can be in a patient and the patient have an angiogenesis-related condition.

As used herein, VEGF is an abbreviation for Vascular Endothelial Growth Factor, and VEGFR is an abbreviation for Vascular Endothelial Growth Factor Receptor. There are three types of VEGFR, namely, VEGFR-1 (also known as Flt), VEGFR-2 (also known as KDR or Flt), and VEGFR-3 (also known as Flt-4), all of which have tyrosine-kinase activity.

As used herein, the term "signal retention peptide" or "peptide retention Signal" refers to an amino acid sequence that binds to retention receptors to prevent secretion of ligands of proteins coupled to such signal retention peptide. In one embodiment, the signal retention peptide binds endoplasmic reticulum retention receptors. In further embodiments, the signal retention peptide of the present invention binds endoplasmic reticulum retention receptors, preventing secretion of a ligand that binds to a receptor. In additional embodiments, the ligand that binds to a receptor is itself at least a portion of a receptor; such chimeric polypeptides comprising a signal retention peptide and at least a portion of a receptor are referred to herein as "intraceptors". It is contemplated that the signal retention peptide of the present invention has the amino acid sequence Lys-Asp-Glu-Leu (KDEL; SEQ ID NO:1), which binds ER retention, receptors, preventing secretion of ligands of proteins coupled to KDEL (SEQ ID NO: 1). In further embodiments, the signal retention peptide is selected from the group consisting of KDEL (SEQ ID NO:1), RDEL (SEQ ID NO:7), and HDEL (SEQ ID NO:8).

As used herein, the intraceptors of the present invention is preferably produced by recombinant DNA techniques. For example, a nucleic acid molecule encoding an intraceptor is cloned into an expression vector, the expression vector is introduced into a host cell, and the intraceptor is expressed in the host cell. The intraceptor can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, the intraceptor of the present invention can be synthesized chemically using standard peptide synthesis techniques. Moreover, native polypeptides for the intraceptor of the present invention, e.g., Flt and/or domains 2 and 3 or domains 2-4, can be isolated from cells (e.g., human cells), for example using an anti-Flt, anti-Flt23, or anti-Flt24 polypeptide antibody.

As used herein, the term "nucleotide" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene; at least about 1000 nucleotides of sequence upstream from the 5' end of the coding region and at least about 200 nucleotides of sequence downstream item the 3' end of the coding region, of the gene. Less common bases, such as inosine, 5-methykytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid or polynucleotide molecule is one that is substantially separated from other nucleic acid molecules, which are present in the natural source of the nucleic acid (i.e., sequences encoding other polypeptides). Preferably, an "isolated" nucleic acid is free of some of the sequences. Which naturally flank the nucleic acid (i.e. sequences located at the 5' and 3' ends of the nucleic acid) in its naturally occurring replicon. For example, a cloned nucleic acid is considered isolated. In various embodiments, the isolated intraceptor nucleic acid molecule can contain, less than about 5 kb, 4 kb, 3 kb, 2 Kb, 1 kb, 0.5 kb, or 0.1 kb of nucleotide sequences which naturally flank the nucleic acid molecule in genomic DNA of the cell from which the nucleic acid is derived (e.g., a human or rat cell). A nucleic acid is also considered isolated if it has been altered by human intervention, or placed in a locus or location that is not its natural site. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-ocurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid mates up less than 5% of the number of nucleic acid inserts in the vector molecules. Further specifically excluded are whole cell genomic DNA or whole cell RNA preparations (including whole cell preparations that are mechanically sheared or enzymatically digested). Even farther specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single hand from a heterogeneous band, population in an agarose gel or nylon blot).

A nucleic acid molecule of the present invention, or a portion thereof, can be isolated using standard molecular biology techniques and the sequence information provided herein, for example, a cDNA for domains 2 and 3 or domains 2, 3, and 4 of Flt can be isolated from a cDNA library using all or portion of one of the sequences encoding Flt23 (nucleotides 1-633 of SEQ ID NO:3) or Flt24 (nuceotides 1-915 of SEQ ID NO:5). Moreover, a nucleic acid molecule encompassing all or a portion of Flt23 (nucleotides 1-633 of SEQ ID NO:3), or Flt24 (nucleotides 1-915 of SEQ ID NO:5) can be isolated by the polymerase chain reaction (PCR) using oligonucleotide primers designed based upon the sequences. For example, mRNA can be isolated from a cell, and synthetic oligonucleotide primers for PCR amplification can be designed based upon one of the nucleotide sequences of Flt23 (nucleotides 1-633 of SEQ ID NO:3), or Flt24 (nucleotides 1-915 of SEQ ID NO: 5). A nucleic acid molecule of the present invention can be amplified using cDNA or, alternatively, genomic DNA, as a template and appropriate oligonucleotide primers according to standard PCR amplification techniques. The nucleic acid molecule so amplified can be cloned into an appropriate vector and characterised by DNA sequence analysis. Furthermore, oligonucleotides corresponding to these nucleotide sequences can be prepared by standard synthetic techniques, e.g., using an automated DNA synthesizer.

The present invention provides an isolated nucleic acid, wherein the nucleic acid comprises a polynucleotide selected from the group consisting of: a) a polynucleotide as defined in SEQ ID NO:3; b) a polynucleotide as defined in SEQ ID NO:5; c) a polynucleotide encoding a polypeptide as defined in SEQ ID NO:4; d) a polynucleotide encoding a polypeptide as defined in SEQ ID NO:6; and e) a polynucleotide complementary to a full-length polynucleotide of any one of a) through d) above. In one embodiment, an isolated nucleic acid molecule of the present invention comprises one of the polynucleotide sequences shown in SEQ ID NO:3 or SEQ ID NO:5. In another preferred embodiment, an isolated nucleic acid molecule of the present invention comprises a polynucleotide sequence encoding a polypeptide as shown in SEQ ID NO:4 or SEQ ID NO:6. In yet another embodiment, the invention provides an isolated nucleic acid comprising a polynucleotide encoding a polypeptide having at least 80% sequence identity with a polypeptide as shown in SEQ ID NO:4 or SEQ ID NO:6, and wherein the nucleic acid may interacts with VEGF and/or a VEGFR. and can decrease the activity of VEGF and/or the VEGFR in a further embodiment, the invention provides an isolated nucleic acid, wherein the nucleic acid comprises a polynucleotide that hybridizes under highly stringent conditions to a second nucleic acid selected from the group consisting of: a) a polynucleotide as defined in SEQ ID NO: 3 or SEQ ID NO:5; and b) a polynucleotide encoding a polypeptide as defined in SEQ ID NO:4 or SEQ ID NO:6, wherein said nucleic acid encodes a polypeptide that interacts with VEGF and/or VEGFR-2, and wherein the stringent conditions comprise hybridization in a 6X SSC solution at 65° C. In one embodiment of the present invention, the isolated nucleic acids encode a polypeptide that is capable of interacting with VEGF and/or a VEGFR.

Moreover, the nucleic acid molecule of the present invention can comprise a portion, of one of the sequences of Flt23 (nucleotides 1-633 of SEQ ID NO:3) or Flt24 (nucleotides 1-915 of SEQ ID NO:5), for example, a fragment that can be used as a probe or primer or a fragment encoding a biologically active portion of the intraceptor of the present invention. The nucleotide sequences determined from the cloning of the VEGF, and/or VEGFR genes from human cells allow for the generation of probes and primers designed for use in identifying and cloning the intraceptor homologs from other cell types and organisms.

As used herein, the term "biologically active portion of" the intraceptor polypeptide is intended to include a portion, e.g., a domain/motif, of a Flt23 (amino acids 1-211 of SEQ ID NO:4), or Flt24 (amino acids 1-305 of SEQ ID NO:6) polypeptide that participates in the interaction with of the intraceptor with VEGF and/or a VEGFR. Biologically active portions of a Flt23 (amino acids 1-211 of SEQ ID NO:4), or Flt24 (amino acids 1-305 of SEQ ID NO:6) polypeptide include peptides comprising amino acid sequences derived from the amino acid sequence of a Flt23 (amino acids 1-211 of SEQ ID NO:4), or Flt24 (amino acids 1-305 of SEQ ID NO:6) polypeptide, or the amino acid sequence of a polypeptide identical to a Flt23 (amino acids 1-211 of SEQ ID NO:4), or Flt24 (ammo acids 1-305 of SEQ ID NO:6) polypeptide which include fewer amino acids than a full length of those polypeptides, or the full length polypeptide which is identical to a Flt23 (amino acids 1-211 of SEQ ID NO:4), or Flt24 (ammo acids 1-305 of SEQ ID NO: 6) polypeptide, and exhibit at least one activity of a Flt23 (amino acids 1-211 of SEQ ID NO:4), or Flt24 (amino acids 1-305 of SEQ ID NO:6) polypeptide. Typically, biologically active portions (e.g., peptides which, ate, for example, 5, 10, 15, 20, 30, 35, 36, 37, 38, 39, 40, 50, 60, 70, 80, 90, or more amino acids in length) comprise a domain or motif with at least one activity of a Flt polypeptide. As used herein, the term "activity" is intended to Include, but is not limited to, the interaction with a VEGFR or VEGF to modulate VEGF signaling. As also used herein, the term "interaction with a VEGFR or VEGF" is intended to include, but is not limited to, the binding of the intraceptors of the present Invention to a VEGFR. or to VEGF to sequester the protein, or decrease the expression or secretion of the VEGF and/or VEGFR.

The present invention also provides intraceptors, e.g., Flt23K (SEQ ID NO:4) or Flt24R (SEQ ID NO:6), comprising chimeric or fusion polypeptides. As used herein, a "chimeric polypeptide" or "fusion polypeptide" comprises at least a portion of an extracellular receptor operatively linked to another substantially different peptide. One of the intraceptors of the present invention, namely, Flt23K polypeptide (SEQ ID NO:4), refers to a polypeptide having an amino acid sequence corresponding to domains 2 and 3 of VEGFR (Flt) polypeptide (amino acids 1-211 of SEQ ID NO:4), and a signal retention peptide having an amino acid sequence Lys-Asp-Glu-Leu (KDEL; SEQ ID NO:1). Another intraceptor of the present invention, namely, Flt24K polypeptide (SEQ ID NO:6), refers to a polypeptide having an amino acid sequence corresponding to domains 2, 3-and 4 of VEGFR-1 (Flt) polypeptide (amino acids 1-305 of SEQ ID NO:6), and a signal retention peptide KDEL (SEQ ID NO:1. As used herein, the term "operatively linked" is intended to indicate mat the Flt23 (amino acids 1-211 of SEQ ID NO:4) or Flt24 (amino acids 1-30.5 of SEQ ID NO:6) polypeptide and the signal retention peptide, KDEL (SEQ ID NO: 1), are fused to each other so that both sequences fulfill the proposed function attributed to the sequence used. The signal retention peptide can be fused to the N-terminus or C-terminus of the VEGFR-1 polypeptide. For example, in one embodiment, the intraceptors of the present invention are fusion polypeptides, Flt23-KDEL (Flt23K; SEQ ID NO:4) and Flt24-KDEL (Flt24K; SEQ ID NO:6), in which the Flt23 (amino acids 1-213 of SEQ ID NO:4) or Flt24 (amino acids 1-305 of SEQ ID NO:6) sequences are fused with KDEL (SEQ ID NO:1) at the C-terminus.

The invention further encompasses an intraceptor comprising a polypeptide encoded by a nucleotide sequence encoding at least a portion of an extracellular receptor, operatively linked to a signal retention, peptide. As used herein, "extracellular receptor" refers to a receptor that has an extracellular domain. Such receptors can also have transmembrane and intracellular domains, or can be otherwise tethered to the cell. Non-limiting examples of extracellular receptors include receptor kinases such as EGF or TGF-beta receptors, G-coupled protein receptors such as the V2vasopressin receptor, and ligand-gated ion channels such as the nicotinic cholinergic receptor.

Preferably, the intraceptors of the present invention comprising a chimeric or fusion polypeptide are produced by standard recombinant DNA techniques. For example, DNA fragments coding for the different polypeptide sequences are ligated together in-frame in accordance with conventional techniques, for example by employing blunt-ended, or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and re-amplified to generate a chimeric gene sequence (See, for example, Current Protocols in Molecular Biology, Eds. Ausubel et al. John Wiley & Sons: 1992), Moreover, many expression vectors are commercially available that already encode a fusion moiety.

In addition to fragments and fusion polypeptides of the intraceptors described herein, the present invention includes homologs and analogs of naturally occurring Flt23 (amino acids 1-211 of SEQ ID NO:4) or Flt24 (amino acids 1-305 of SEQ ID NO:6) polypeptides and Flt3 (nucleotides 1-633 of SEQ ID NO:3) or Flt24 (nucleotides 1-915 of SEQ ID NO: 5) encoding nucleic acids in the same or other organisms. "Homologs" are defined herein as two nucleic acids or polypeptides that have similar or "identical," nucleotide or amino acid sequences, respectively. Homologs include allelic variants, orthologs, paralogs, agonists, and antagonists of Flt23 (amino acids 1-211 of SEQ ID NO:4) and Flt24 (amino acids 1-305 of SEQ ID NO:6) polypeptides as defined hereafter. The term "homolog" further encompasses nucleic acid molecules that differ from one of the nucleotide sequence of Flt (SEQ ID NO: 12), Flt23 (nucleotides 1-633 of SEQ ID NO:3), or Flt24 (nucleotides 1-915 of SEQ ID NO: 5) (and portions thereof) due to degeneracy of the genetic code and thus encode the same Flt23, Flt24, Flt23K or Flt24K polypeptide as that encoded by the nucleotide sequences shown in SEQ ID NO:3 or SEQ ID NO:5, or portions thereof. As used herein, a "naturally occurring" Flt23 (amino acids 1-211 of SEQ ID NO:4) or Flt24 (amino acids 1-305 of SEQ ID NO: 6) polypeptide refers to a Flt23 or Flt24 amino acid sequence that occurs in nature. Preferably, a naturally occurring Flt23 or Flt24 polypeptide comprises an amino acid sequence as defined in SEQ ID NO:4 or SEQ ID NO:6 minus the KDEL (SEQ ID NO:1) sequence at the C-terminal.

Art agonist of the intraceptors of the present invention can retain substantially the same, or a subset, of the biological activities of the intraceptors of the present invention. An antagonist of the intraceptors of the present invention polypeptide can inhibit one or more of the activities of the intraceptor.

Nucleic acid molecules corresponding to natural allelic variants and analogs, orthologs, and paralogs of a Flt (SEQ ID NO: 12), Flt23 (nucleotides 1-633 of SEQ ID NO:3) or Flt24 (nucleotides 1-915 of SEQ ID NO: 5) cDNA can be isolated based on their identity to the Flt, Flt23 or Flt24 nucleic acids described herein using Flt, Flt23 or Flt24 cDNAs, or a portion thereof, as a hybridization probe according to standard hybridization techniques under stringent hybridization conditions. In an alternative embodiment, homologs of the Flt, Flt23 or Flt24 polypeptide can be identified by screening combinatorial libraries of mutants, e.g., truncation mutants, of the Flt, Flt23, or Flt24, for Flt, Flt23 or Flt24 agonist or antagonist activity. In one embodiment, a variegated library of Flt, Flt23 or Flt24 variants is generated by combinatorial mutagenesis at the nucleic acid level and is encoded by a variegated gene library. A variegated library of Flt, Flt23, or Flt24 variants can be produced by, for example, enzymatically ligating a mixture of synthetic oligonucleotides into gene sequences such that a degenerate set of potential Flt, Flt23 or Flt24 sequences is expressible as individual polypeptides, or alternatively, as a set of larger fusion polypeptides (e.g., for phage display) containing the set of Flt, Flt23 or Flt24 sequences therein. There are a variety of methods that can be used to produce libraries of potential Flt, Flt23 or Flt24 homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential Flt, Flt23 or Flt24 sequences. Methods for synthesizing degenerate oligonucleotides are known in the art (See, e.g., Narang, 1983, Tetrahedron 39:3; Itakura et al., 1984, Annu. Rev. Biochem 53:323; Itakura et al., 1984, Science 198: 1056; Ike et al., 1983, Nucleic Acid Res. 11:477).

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of Flt, Flt23 or Flt24 homologs. The most widely used techniques, which are amenable to high through-put analysis, for screening large gene libraries typically include cloning the gene library into replicable expression vectors, transforming appropriate cells with the resulting library of vectors, and expressing fee combinatorial genes under conditions in which detention of a desired activity facilitates isolation of the vector encoding the gene whose product was detected. Recursive ensemble mutagenesis (REM), a technique that enhances the frequency of functional mutants in the libraries, can be used in combination with the screening assays to identify Flt, Flt23 or Flt24 homologs (Arkin & Yourvan, 1992, PNAS 89:7811-7315; Delgrave et al., 1993, Polypeptide Engineering 6(3): 327-331), As stated above, the present invention includes intraceptors, e.g, Flt23K (SEQ ID NO:4) and Flt24 (SEQ ID NO:6), which comprise Flt23 and Flt24 polypeptides operatively linked to a signal retention peptide, and homologs thereof. To determine the percent sequence identity of two amino acid sequences, the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences.

The percent sequence identity between the two sequences is a function of the number of identical positions shared by the sequences (i.e., percent sequence identity =numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%. or 90-95%, and most preferably at least about 96%, 97%, 98%, 99%, or more identical to an entire amino acid sequence of Flt23 (amino acids 1-211 of SEQ ID NO:4) or Flt24 (amino acids 1-305 of SEQ ID NO: 6). In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence of Flt23 (nucleotides 1-633 of SEQ ID NO:3) or Flt24 (nucleotides 1-915 of SEQ ID NO:5). In other embodiments, the amino acid homologs have sequence identity over at least 15 contiguous amino acid residues, more preferably at least 25 contiguous amino acid residues, and most preferably at least 35 contiguous amino acid residues of Flt23 (amino acids 1-211 of SEQ ID NO:4) or Flt24 (amino acids 1-305 of SEQ ID NO:6). In another embodiment, the homologs of the present invention are preferably at least about 60-70%, and more preferably at least about: 80-85%, 85-90%, or 90-95%, and most preferably at least about 96%, 97%, 98%, 99%, or more identical to Flt23 (amino acids 1-211 of SEQ ID NO:4) or Flt24 (amino acids 1-305 of SEQ ID NO:6).

In another preferred embodiment, an isolated nucleic acid homolog of the invention comprises a nucleotide sequence which is at least about 60-70%, more preferably at least about 70-75%, 75-89%, 80-85%, 85-99%, or 90-95%, and even more preferably at least about 95%, 96%, 97%, 98%, 99%, or more identical to a nucleotide sequence of Flt23 (nucleotides 1-633 of SEQ ID NO:3) or Flt24 (nucleotides 1-915 of SEQ ID NO: 5), or to a portion comprising at least 60 consecutive nucleotides thereof. In one embodiment, the Flt23 or Flt24 homolog nucleotide sequence is about 80-90% identical to a nucleotide sequence of Flt23 (nucleotides 1-633 of SEQ ID NO:3) or Flt24 (nucleotides 1-915 of SEQ ID NO:5). The preferable length of sequence comparison for nucleic acids is at least 75 nucleotides, more preferably at least 100 nucleotides, and most preferably entire length of the coding region for Flt23 or Flt24. It is even more preferable that the nucleic acid homologs encode proteins having homology with Flt23 (amino acids 1-211 of SEQ ID NO:4) or Flt24 (amino acids 1-305 of SEQ ID NO:6).

It is further preferred that the isolated nucleic acid homolog of the invention encodes a Flt33 or Flt24, or portion thereof, that is at least 80% identical to an amino acid sequence of Flt23 (amino acids 1-211 of SEQ ID NO:4) or Flt24 (amino acids 1-305 of SEQ ID NO:6), and that, after coupled with a signal retention peptide, KDEL (SEQ ID NO:1), may function by interacting with a VEGF and/or a VEGFR to thereby disrupt the VEGF signaling pathway.

For the purposes of the invention, the percent sequence identify between two nucleic acid or polypeptide sequences is determined using the Vector NTI 6.0 (PC) software package (InforMax, 7600 Wisconsin Ave., Sethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to he understood that for the purposes of determining sequence identity when comparing a DNA sequence to an RNA sequence, a thymidine nucleotide is equivalent to a uracil nucleotide.

In another aspect, the invention provides an intraceptor encoded by an isolated nucleic acid comprising a polynucleotide that hybridizes to the polynucleotide of Flt23 (nucleotides 1-633 of SEQ ID NO:3) or Flt24 (nucleotides 1-915 of SEQ ID NO: 5) under stringent conditions. More particularly, an isolated nucleic acid molecule of the invention is at least 15 nucleotides in length and hybridizes under stringent conditions to the nucleic acid molecule comprising a nucleotide sequence of Flt23 (nucleotides 1-633 of SEQ ID NO:3) or Flt24 (nucleotides 1-915 of SEQ ID NO:5). In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence of Flt23 (nucleotides 1-633 of SEQ ID NO:3) or Flt24 (nucleotides 1-915 of SEQ ID NO: 5), and after coupled with a signal retention peptide, it may be used, to interact with, a VEGF and/or VEGFR for the treatment of angiogenesis.

As used herein with regard to hybridization for DNA to a DNA blot, the term "stringent conditions" refers to hybridization overnight at 6° C. in 10× Denhardt's solution, 6× SSC, 0.5% SDS, and 100 µg/ml denatured salmon sperm DNA, Blots are washed sequentially at 65° C. for 30 minutes each time in 3× SSC/0.1% SDS, followed by 1× SSC/0.1% SDS, and finally 0.1× SSC/0.1% SDS. As also used herein, "highly stringent conditions" refers to hybridization overnight at 65° C. in 10× Denhardt's solution, 6× SSC, 0.5% SDS, and 100 µg/ml denatured salmon sperm DNA. Blots are washed sequentially at 65° C. for 30 minutes each time in 3× SSC/0.1% SDS, followed by 1× SSC/0.1% SDS, and finally 0.1× SSC/0.1% SDS. In another embodiment, "highly stringent conditions" refers to hybridization at 65° C. in a 6× SSC solution. Methods for nucleic acid hybridizations are described in Meinkoth and Wahl 1984, Anal. Biochem. 138: 267-284; Current .Protocols in Molecular Biology, Chapter 2, Asusubel et al., Greene Publishing and Wiley-Interscience, New York, 1995; and Tijssen, 1993, Laboratory Techniques in Biochemistry and Molecular Biology; Hybridization with Nucleic Acid Probes, Part 1 Chapter 2, Elsevier, New York, 1993. Preferably, an isolated nucleic acid molecule of tins invention that hybridizes under stringent or highly stringent conditions to a sequence of Flt23 (nucleotides 1-633 of SEQ ID NO:3) or Flt24 (nucleotides 1-915 of SEQ ID NO:5) corresponds to a naturally occurring nucleic acid molecule. As used herein, a "naturally occurring" nucleic acid molecule refers to an RNA or DNA molecule having a nucleotide sequence that occurs in nature (e.g., encodes a natural, polypeptide).

Using the above-described methods, and others known to those of skill is the art, one of ordinary skill in the art can isolate homologs of Flt23 or Flt24 polypeptides comprising amino acid sequences of Flt23 (amino acids 1-211 of SEQ ID NO:4) or Flt24 (amino acids 1-305 of SEQ ID NO:6), respectively. One subset of these homologs is allelic variants. As used herein, the term, "allelic variant" refers to a nucleotide sequence containing polymorphisms that lead to changes in the amino acid sequences of Flt23 (amino acids 1-211 of SEQ ID NO:4) or Flt24 (amino acids 1-305 of SEQ ID NO:6) and that exist within a natural population, Such natural allelic variations can typically result in 1-5% variance in a Flt23 or Flt24 nucleic acid. Allelic variants can be identified by sequencing the nucleic acid sequence of interest in a number of different organisms, which can be readily carried out by using hybridization probes to identify the same Flt23 or Flt24 genetic locus in those organisms. Any and all such nucleic acid variations and resulting amino acid polymorphisms or variations in a Flt23 or Flt24 polypeptide that are the result of natural allelic variation and that do not alter the functional activity of a Flt23 or Flt24 polypeptide, are intended to be within the scope of the invention.

Moreover, nucleic acid molecules encoding Flt23 or Flt24 polypeptides from, the same or other species such as Flt23 or Flt24 analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov, R. L. et al., 1997, Science 278(5338):631-637). Analogs, orthologs, and paralogs of a naturally occurring Flt23 or Flt24 polypeptide can differ from the naturally occurring Flt23 or Flt24 polypeptide by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring Flt23 or Flt24 amino acid sequence, and will exhibit a function similar to a Flt23 or Flt24 polypeptide. Preferably, a Flt23 or Flt24 ortholog of the present invention is encoded by a nucleic acid that may be used to interact with VEGF and/or a VEGFR to thereby disrupt the VEGF signaling pathway.

In addition to naturally-occurring variants of a Flt, Flt23 or Flt24 sequence that may exist in the population, the skilled artisan will further appreciate that changes can be introduced by mutation into a nucleotide sequence of Flt, Flt23 or Flt24, thereby leading to changes in the amino acid sequence of the encoded Flt, Flt23 or Flt24polypeptide, without altering the functional activity of the Flt, Flt23 or Flt24polypeptide. For example, nucleotide substitutions leading to amino acid substitutions at "non-essential" amino acid residues can be made in a sequence of Flt, Flt23 or Flt24. A "non-essential" amino acid residue is a residue that can be altered from the wild-type sequence of one of the Flt, Flt23 or Flt24 polypeptides without altering the activity of said Flt, Flt23 or Flt24 polypeptide, whereas an "essential" amino acid residue is required for Flt, Flt23 or Flt4 activity. Other amino acid residues, however, (e.g., those that are not conserved or only semi-conserved in the domain having Flt, Flt23 or Flt24 activity) may not he essential for activity and thus are likely to be amenable to alteration without altering Flt, Flt23 or Flt24 activity.

Accordingly, another aspect of the invention pertains to nucleic acid molecules encoding Flt, Flt23 or Flt24 polypeptides coupled with a signal retention peptide, such as KDEL (SEQ ID NO:1), RDEL (SEQ ID NO:7), or HDEL (SEQ ID NO:8), wherein the Flt, Flt23 or Flt24 polypeptides contain changes in amino acid residues that are not essential tor Flt, Flt23 or Flt24 activity. Such Flt, Flt23 or Flt24polypeptides may have different amino acid sequence, yet retain at least one of the Flt Flt23 or Flt24 activities described herein, in one embodiment, the isolated nucleic add molecule comprises a nucleotide sequence encoding a polypeptide, wherein the polypeptide comprises an amino acid sequence at least about 89% identical to an amino acid sequence of Flt (SEQ ID NO:13), Flt23 (amino acids 1-211 of SEQ ID NO:4) or Flt24 (amino acids 1-305 of SEQ ID NO:6). Preferably, the polypeptide encoded by the nucleic-acid molecule is at least about 80-85% identical to one of the sequences of Flt (SEQ ID NO:13), Flt23 (amino acids 1-211 of SEQ ID NO:4) or Flt24 (amino acids 1-305 of SEQ ID NO:6), more preferably at least about 88-90% or 90-95% identical to one of the sequences of Flt (SEQ ID NO:13), Flt23 (amino acids 1-211 of SEQ ID NO:4) or Flt24 (amino acids 1-305 of SEQ ID NO:6), and most preferably at least about 96%, 97%, 98%, or 99% identical to one of the sequences of Flt (SEQ ID NO:13), Flt23 (amino acids 1-211 of SEQ ID NO:4) or Flt24 (amino acids 1-365 of SEQ ID NO:6).

The intraceptors of the present invention, Flt23K (SEQ ID NO:4) or Flt24K (SEQ ID NO:6), encoded by an isolated nucleic acid molecule having sequence identity with a polypeptide sequence of Flt, Flt23, Flt24, Flt23K, or Flt24K can be created by introducing one or more nucleotide substitutions, additions or deletions into a nucleotide sequence of Flt (SEQ ID NO: 12 or 13), Flt23 (nucleotides 1-633 of SEQ ID NO:3) or Flt24 (nucleotides 1-915 of SEQ ID NO:5), respectively, such that one or more amino acid substitutions, additions, or deletions are introduced into the encoded polypeptide. Mutations can be introduced into one of the sequences of Flt (SEQ ID NO: 12 or 13), Flt23 (nucleotides 1-633 of SEQ ID NO:3), Flt24 (nucleotides 1-915 of SEQ ID NO:5), Flt23K (SEQ ID NO:3) or Flt24K (SEQ ID NO:5) by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in a Flt (SEQ ID NO:13), Flt23 (amino acids 1-211 of SEQ ID NO:4), Flt24 (amino acids 1-305 of SEQ ID NO:6), Flt23K (SEQ ID NO:4) or Flt24K (SEQ ID NO:6) polypeptide is preferably replaced with another amino acid residue from the same side chain family. Alternatively, in another embodiment, mutations can be introduced randomly along all or part of a Flt, Flt23, Flt24, Flt23K, or Flt24K sequence, such, as by saturation mutagenesis, and the resultant mutants can be screened for a Flt. Flt23, Flt24, Flt23K or Flt24K activity described herein to identify mutants that retain the activity. Following mutagenesis of one of the sequences of Flt, Flt23, Flt24, Flt23K, Flt24K, the encoded polypeptide can be expressed recombinantly and the activity of the polypeptide can be determined.

Additionally, optimized nucleic acids encoding intraceptors can be created. Preferably, an optimised nucleic acid encodes an intraceptor comprising a Flt23 or Flt24 polypeptide coupled with signal retention polypeptide feat binds to VEGF and/or a VEGFR and, in one embodiment suppresses the expression and/or secretion of VEGF or the VEGFR. As used herein, "optimized" refers to a nucleic acid that is genetically engineered, to increase its expression in a given organism. To provide optimised intraceptor nucleic acids (e.g., Flt23K, (SEQ ID NO:3) and Flt24K, (SEQ ID NO:5), the DNA sequence of the gene can be modified to 1) comprise codons preferred by highly expressed genes in the organism; 2) comprise an A+T content in nucleotide base composition to that substantially found in the organism; 3) form an initiation sequence for that organism; or 4) to eliminate sequences that cause destabilization, inappropriate polyadenylation, degradation and termination of RNA, or that form secondary structure hairpins or RNA splice sites. Increased expression of intraceptor nucleic acids (e.g. Flt23K (SEQ ID NO:3) and Flt24K: (SEQ ID NO:5)) in an organism can be achieved by utilizing the distribution frequency of codon usage in a particular organism.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell it is preferable that ibis analysis be limited to genes that are highly expressed by the host cell. The percent deviation of the frequency of preferred codon usage for a synthetic gene from that employed by a host cell is calculated first by determining the percent deviation of the frequency of usage of a single codon front that of the host cell followed by obtaining the average deviation over all codons. As defined herein, this calculation includes unique codons (i.e., ATG and TGG). In general terms, the overall average deviation of the codon usage of an optimized gene from, that of a host cell is calculated using the equation $1A=n=1\ Z\ X_n-Y_n\ X_n$ times $100\ Z$ where $X_n$=frequency of usage for codon n in the host cell; $Y_n$=frequency of usage for codon n in the synthetic gene; n represents an individual codon that specifies an amino acid; and the total number of codons is Z. The overall deviation of the frequency of codon usage. A, for all amino acids should preferably be less than, about 25%, and more preferably less than about 10%.

Hence, an intraceptor nucleic acid, e.g. Flt23K (SEQ ID NO:3) and Flt24K (SEQ ID NO:5) can he optimized such that its distribution frequency of codon usage deviates, preferably, no more than 25% from that of highly expressed genes in that organism and, more preferably, no more than about 10%. In addition, consideration is given to the percentage G+C content of the degenerate third base.

In addition to the intraceptor nucleic acids, Flt23K, SEQ ID NO:3 and Flt24K, SEQ ID NO:5, and their encoding polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. As used herein, the terms "probe" and "primer" are intended to include oligonucleotides that typically comprise a region of nucleotide sequence that hybridizes under stringent conditions to at least about 12, preferably about 25, more preferably about 40, 50, or 75 consecutive nucleotides of a sense strand of one of the sequences of Flt (SEQ ID NO: 12 or 13). Flt23 (nucleotides 1-633 of SEQ ID NO:3), Flt24 (nucleotides 1-915 of SEQ ID NO:5), Flt23K (SEQ ID NO:3), or Flt24 (SEQ ID NO:5); an anti-sense sequence of one of the sequences of Flt (SEQ ID NO:12 or 13), Flt23 (nucleotides 1-633 of SEQ ID NO:3), Flt24 (nucleotides 1-915 of SEQ ID NO:5), Flt23K (SEQ ID NO:3), or Flt24K (SEQ ID NO:5); or naturally occurring mutants thereof. Primers based on a nucleotide sequence of Flt (SEQ ID NO: 12 or 13), Flt23 (nucleotides 1-633 of SEQ ID NO:3), Flt24 (nucleotides 1-915 of SEQ ID NO:5), Flt23K (SEQ ID NO:3), or Flt24K (SEQ ID NO:5) can be used in PCR reactions to clone Flt (SEQ ID NO: 12 or 13), Flt23 (nucleotides 1-633 of SEQ ID NO:3), Flt24 (nucleotides 1-915 of SEQ ID NO:5), Flt23K (SEQ ID NO:3), or Flt24K (SEQ ID NO:5) homologs. Probes based on these nucleotide sequences can be used to detect transcripts or genomic sequences encoding the same or substantially identical polypeptides. In preferred embodiments, the probe further comprises a label group attached thereto, e.g. the label group can be a radioisotope, a bioluminescent compound, a chemiluminescent compound, a metal chelate, a fluorescent compound, an enzyme, or an enzyme co-factor.

In particular, a useful method to ascertain the level of transcription, of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA cart be prepared from cells, tissues, or organs by several methods, all well-known in the art, such as that described, in Bormann E. R. et al., 1992, Mol. Microbiol 6:317-326. To assess tire presence or relative quantity of polypeptide translated from this mRNA, standard techniques, such as a Western blot, may be employed. These techniques are well known to one of ordinary skill in the art. (See, for example, Ausubel et al. 1988, Current Protocols in Molecular Biology, Wiley: New York).

The invention further provides an isolated recombinant expression vector comprising the intraceptor nucleic acids as described above, wherein expression of the intraceptor nucleic acid in. a host cell results in modulation of VEGF and/or VEGFR activity as compared to a wild type variety of the host cell. As used herein, the term "vector" refers to a nucleic acid molecule capable of transporting another nucleic acid to which it has been linked. One type of vector is a "plasmid." which refers to a circular double stranded DNA loop into which additional DMA segments can be ligated. Another type of vector is a viral vector, wherein additional DNA segments can be ligated into the viral genome. Certain vectors are capable of autonomous replication in a host, cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors" In general, expression vectors of utility In. recombinant DNA techniques are often in the form of plasmids. In the present specification, "plasmid" and "vector" can be used interchangeably as fee plasmid is the most commonly uses form of vector. However, the invention is intended to include such other forms of expression vectors, such as viral vectors (e.g., replication detective retroviruses, adenoviruses, and adeno-associated viruses), which serve equivalent functions.

The recombinant expression vectors of the invention, comprise the nucleic acid for the intraceptors of the present invention in a form suitable for expression of the nucleic acid, in a host cell, which means that the recombinant expression, vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequencers) in a manner which allows for expression, of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by these skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., Flt23, Flt24, Flt23K, Flt24K polypeptides, mutant forms or variants thereof).

The recombinant expression, vectors of the invention can be designed for expression of intraceptor polypeptides in prokaryotic or eukaryotic cells. For example, intraceptor Flt23K (SEQ ID NO: 3) or Flt24K (SEQ ID NO: 5) genes can be expressed in bacterial cells such as *C. glutamicum*, insect cells (using baculovirus expression vectors), yeast and other fungal cells (See Romanos, M. A. et al., 1992, Foreign gene expression in yeast: a review. Yeast 8:423-488; van den Hondel, C.A.M.J.J. et al., 1991, Heterologous gene expression in filamentous fungi, in: More Gene Manipulations in Fungi, J. W. Bonnet & L. L. Lasure, eds., p. 396-428: Academic Press: San Diego; and van. den Hondel, C.A.M.J.J. & Punt, P. J., 1991, Gene transfer systems and vector development for filamentous fungi, in: Applied Molecular Genetics of Fungi, Peberdy, J. F. et al., eds., p. 1-28, Cambridge University Press: Cambridge), algae (Falciatore et al. 1999, Marine Biotechnology 1(3):239-251), ciliates of the types: Holotrichia, Peritrichta, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus Stylonychia lemnae with vectors following a transformation method as described in PCT Application No. WO 98/01572, and multicellular plant cells (See Schmidt, R, and Willmitzer, L., 1988, High efficiency *Agrobacterium tumefaciens*-mediated transformation of *Arabidopsis thaliana* leaf and cotyledon explants. Plant Cell Rep. 583-586; Plant Molecular Biology and Biotechnology, C Press, Boca Raton, Fla., chapter 6/7, S.71-119 (1-993); F. F. White, B. Jenes et al., Techniques for Gene Transfer, in: Transgenic Plants, Vol. 1, Engineering and Utilizations eds, Kung und R. Wu, 128-43, Academic Press; 1993; Potrykus, 1991, Annu. Rev. Plant Physiol. Plant Molec. Biol, 42:205-225 and references cited therein), or mammalian cells. Suitable host cells are discussed further in Goeddel, Gene Expression Technology: Methods in Enzymology 185, Academic Press: San Diego, Calif. (1990). Alternatively, the recombinant expression, vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion, vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith, D. B. and Johnson, K. S., 1988, Gene 67:31-40), pMAL, (New England Biolabs, Beverly, Mass.), and pRIT5 (Pharmacia, Piscataway, N.J.) which, fuse glutathione S-tansferase (GST), maltose E binding polypeptide, or polypeptide A, respectively, to the target recombinant polypeptide. In one embodiment, the sequence of the intraceptor of the present invention is cloned into a pCMV expression vector to create a vector encoding the intraceptor fusion polypeptides, Flt23K and Flt24K. The fusion polypeptide can be purified by affinity chromatography.

Examples of suitable inducible non-fusion E. coli expression vectors include pTrc (Amann et al. 1988, Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid, trp-lac fusion promoter. Target gene expression from the pET 11d vector relies on transcription from a T7 gn10-lac fusion promoter mediated by a co-expressed viral RNA polymerase (T7 gnl). This viral polymerase is supplied by host strains BL21(DE3) or HMS174(DE3) from a resident λ prophage harboring a T7 gnl gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, S., Gene Expression Technology: Methods in Enzymology 185, Academic Press, San Diego, Calif. (1990) 119-128). Another strategy is to alter the sequence of the nucleic acid to be inserted into an expression vector so that the individual codons for each amino acid are those preferentially utilised in the bacterium chosen for expression, such as C. glutamicum (Wada et al., 1992, Nucleic Acids Res. 20:2111-2118). Such alteration of nucleic acid sequences of the invention can be carried out by standard DNA synthesis techniques. P In another embodiment, the expression vector expressing the intraceptors of the present invention can be a yeast expression vector. Examples of vectors for expression in yeast S. cerevisiae include pYepSec1 (Baldari, et al., 1987, EMBO J. 6:229-234), pMFa (Kurjan and Herskowitz, 1982, Cell 30:933-943), pJRY88 (Schultz et al., 1987, Gene 54:113-123), and pYES2 (Invitrogen Corporation, San Diego, Calif.). Vector and methods for the construction of vectors appropriate for use in other fungi, such as the filamentous fungi, include those detailed in: van den Hondel, C.A.M.J.J. & Punt, P. J., 1991, "Gene transfer systems and vector development for filamentous fungi," in; Applied Molecular Genetics of Fungi, J. F. Peberdy, et al,. eds, p. 1-28, Cambridge University Press: Cambridge.

Alternatively, the intraceptor polypeptides of the invention can be expressed in insect cells using baculoviras expression vectors. Baculovirus vectors available for expression, of polypeptides in cultured insect cells (e.g., Sf 9 cells) include the pAc series (Smith et al., 1983, Mol. Cell Biol 3:2156-2165) and the pVL series (Lucklow and Summers, 1989, Virology 170:31-39).

In yet another embodiment, the intraceptors of the present invention are expressed in mammalian cells using a mammalian expression vector. Examples of mammalian expression vectors include pCDM8 (Seed, B., 1987, Nature 329: 840) and pMT2PC (Kaufman et. al., 1987, EMBO J. 6:187-195), When used in mammalian, cells, the expression vector's control functions are often provided by viral regulatory elements. For example, commonly used promoters are derived from polyoma, Adenovirus 2, cytomegalovirus, and Simian Virus 40. For other suitable expression systems for both prokuryotic and eukaryotic cells, see chapters 16 and 17 of Sambrook, J., Fritsh, E. F., & Maniatis, T. Molecular Cloning: A Laboratory Manual, latest ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, Genes Dev. 1068-277), lymphoid-specific promoter (Calame and Eaton, 1988, Adv. Immunol. 43:235-275), in particular promoters of T cell receptors (Winoto and Baltimore, 1989, EMBO J. 8:729-733), and immunoglobulins (Banerji et al., 1983, Cell 33:729-740; Queen, and Baltimore, 1983, Cell 33:741-748), neuron-specific promoters (e.g., the neurofilament promoter; Byrne and Ruddle, 1989, PNAS 36:5473-5477), pancreas-specific promoters (Edlund et al., 1985, Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990, Science 249:374-379) and the fetopolypeptide promoter (Campes & Tilghman, 1989, Genes Dev. 3:537-546).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drags, such as G418, hygromycin, and methotrexate. Nucleic acid molecules encoding a selectable marker can be introduced into a host cell on the same vector as that encoding fire intraceptor of the present invention or can be introduced on a separate vector. Cells stably transfected, with the introduced nucleic acid molecule can be identified by, for example, antibiotic selection (e.g., cells that have incorporated the selectable marker gene will survive, while the other cells die).

According to the present invention, the introduced intraceptor polypeptides, may be maintained in the host cell stably if it is incorporated into a non-chromosomal autonomous replicon or integrated into a host cell chromosome. Alternatively, the introduced intraceptor polypeptides may be present on an extra-chromosomal non-replicating vector and may be transiently expressed or transiently active.

Whether present in an extra-chromosomal non-replicating vector or a vector that is integrated into a chromosome, the intraceptor polynucleotides preferably reside in a mammalian expression cassette. A mammalian expression cassette preferably contains regulatory sequences capable of driving gene expression in mammalian cells that are operatively linked so that each sequence can fulfill its function, for example, termination of transcription by polyadenylation signals.

Gene expression should be operatively linked to an appropriate promoter conferring gene expression in a timely, cell specific, or tissue specific manner. Promoters useful in the expression cassettes of the invention include any promoter that is capable of initiating transcription, in a host cell. The promoter may be constitutive, inducible, developmental stage-preferred, cell type-preferred, tissue-preferred, or organ-preferred.

The nucleic acid molecules, polypeptides, polypeptide homologs, fusion polypeptides, primers, vectors, and host cells described herein can be used in one or more of the following methods: evolutionary studies; determination of intraceptor regions required for function; modulation of intraceptor activity; and modulation of VEGF and/or VEGFR activity.

The invention further provides a recombinant expression vector comprising an DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a Flt, Flt23 or Flt24 mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1 (1), and Mol et al., 1990, FEBS Letters 268:427-430.

Another aspect of the invention, pertains to host cells into which a recombinant expression vector of the invention has been introduced. The terms "host cell" and "recombinant host cell" are used interchangeably herein. It is understood that such terms refer not only to the particular subject cell, but they also apply to the progeny of potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or enkaryotic cell. For example, the intraceptor polypeptide can be expressed in bacterial cells such as C. glutamicum, insect cells, fungal cells, or mammalian cells (such as Chinese hamster ovary cells (CHO) or COS cells), algae, dilates, plant cells, fungi, or other microorganisms like C. glutamicum. Other suitable host cells are known to those skilled in the art.

A host, ceil of the invention, such as a prokaryotic or eukaryotic host cell in culture, can be used to produce (i.e., express) an intraceptor polypeptide. Accordingly, the invention further provides methods for producing intraceptor polypeptides, e.g., Flt23K or Flt24K, using the host cells of the invention. In one embodiment, the method comprises culturing the host cell of invention (into which a recombinant expression vector encoding the intraceptor polypeptide has been introduced, or into which genome has been introduced, a gene encoding a wild-type or altered, intraceptor polypeptide) in a suitable medium until the intraceptor polypeptide is produced. In another embodiment, the method further comprises isolating intraceptor polypeptides, e.g., Flt23K, or Flt24K, from the medium or the host cell, The intraceptor nucleic acid molecules of the present invention, are also useful for evolutionary and polypeptide structural studies. By comparing the sequences of the nucleic acid molecules of the present invention to those encoding similar polypeptides from other organisms, the evolutionary relatedness of the organisms can be assessed. Similarly, such a comparison permits an assessment of which regions of the sequence are conserved and which are not, which may aid in determining those regions of the polypeptide that are essential for the functioning of the polypeptide. This type of determination is of value for polypeptide engineering studies and may give an indication of what the polypeptide can tolerate in terms of mutagenesis without losing function.

The present invention also provides a pharmaceutical composition comprising the intraceptors of the invention and a pharmaceutically acceptable carrier. The pharmaceutical compositions of the present invention are used for treating an angiogenesis-related condition by contacting and/or administering the pharmaceutical composition to cells or individuals that have such an angiogenesis-related condition. As used herein, the term "treating" includes to preventing the condition, and/or ameliorating the symptoms of the condition. In certain embodiment, the pharmaceutical composition decreases the expression or secretion of VEGF and/or a VEGFR in a cell that is involved in the angiogenesis-related condition, wherein the intraceptor of the pharmaceutical composition interacts with VEGF and/or a VEGFR, preferably, VEGFR-2, resulting in disruption of intracellular VEGF pathways and/or signalings. The mechanisms of the intraceptor action can include, but are not limited to, a) disruption of a VEGF autocrine loop, b) induction of the unfolded protein response (UPR) in cells which produce VEGF, resulting in selective ER stress, leading to apoptosis of vascular endothelial cells; and c) the formation of heterodimers with VEGFR-2 leading to its sequestration, thus, suppressing physiologic Flt/VEGFR-2 heterodimer formation. The pharmaceutical composition, of the present invention provides high specificity and affinity for the target molecule due to the use of a receptor as the therapeutic substrate.

As used herein, the phrases "pharmaceutically or pharmacologically acceptable" refer to molecular entities and compositions that do not produce an adverse, allergic, or other untoward reaction when administered to an animal, or a human, as appropriate. Veterinary uses are equally included within the invention and "pharmaceutically acceptable" formulations include formulations for both clinical and/or veterinary use. As used herein, "pharmaceutically acceptable carrier" includes any and all solvents, dispersion media, coatings, antibacterial, and antifungal agents, isotonic and absorption delaying agents, and the like. The use of such media and agents for pharmaceutically active substances, is well known in the art. Except insofar as any conventional media or agent is incompatible with the active ingredient, its use in the therapeutic compositions is contemplated. For human administration, preparations should meet sterility, pyrogenicity, and general safety and purity standards as required by FDA Office of Biologics standards. Supplementary active ingredients can also be incorporated into the compositions.

As used herein, the term "augiogenesis-related condition" includes, but is not limited to inflammation, stroke, hemangioma, solid tumors, leukemias, lymphomas, myelomas, metastasis, telangiectasia, psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, placentation, polycystic ovary syndrome, dysfunctional uterine bleeding, endometrial hyperplasia and carcinoma, endometriosis, failed implantation and subnormal foetal growth, myometrial fibroids (uterine leiomyomas) and adenomyosis, ovarian hyperstimulation syndrome, ovarian carcinoma, melanoma, venous ulcers, acne, rosacea, warts, eczema, neurofibromatosis, tuberous sclerosis, and chronic inflammatory disease. In certain, embodiments, the angiogenesis-related condition is selected from the group consisting of melanoma, diabetic retinopathy, and macular degeneration.

As used herein, the term "contacting" or "administering" refers to various means of introducing the pharmaceutical composition into a cell, or into a patient. These means are well known, in the art and may include, for example, injection; tablets, pills, capsules, or other solids for oral administration; nasal solutions or sprays; aerosols, inhalants; topical formulations; liposomal forms; and the like. As used herein, the term "effective amount" refers to an amount that will result in the desired result and may readily he determined by one of ordinary skill in the art.

The pharmaceutical, composition comprising intraceptor polypeptides, nucleic acids, and antibodies of the present invention may be formulated for parenteral administration, e.g., formulated for injection via the intravenous, intramuscular, sub-cutaneous, intrastromal, transdermal, or other such routes. The preparation of an aqueous composition that contains such a protein or antibody as an active ingredient will be known to those of skill in the art in light of the present disclosure. Typically, such, compositions can be prepared as injectables, either as liquid solutions or suspensions; solid forms suitable for using to prepare solutions or suspensions upon the addition, of a liquid, prior to injection can also be prepared; and the preparations can also be emulsified.

The pharmaceutical forms suitable for injectable use include sterile aqueous solutions or dispersions formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such, as bacteria and fungi.

The intraceptor compositions of the present invention can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, fox example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such, preparations should contain a preservative to prevent the growth, of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in fee compositions of agents delaying absorption, for example, aluminum monoslearate, and gelatin.

Prior to or upon formulation, the intraceptor compositions of the present invention should be extensively dialyzed to remove undesired small molecular weight molecules, and/or lyophilized for more ready formulation into a desired vehicle, where appropriate. Sterile injectable solutions are prepared by incorporating the active agents in the required amount in fee appropriate solvent with various of the other ingredients enumerated above, as desired, followed by filter sterilisation. Generally, dispersions are prepared by incorporating the various sterilized active ingredients into a sterile vehicle that contains the basic dispersion medium and fee required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable, pharmaceutical compositions in accordance with the invention will generally include an amount of the polypeptide or nucleic acid admixed with an acceptable pharmaceutical diluent or excipient, such as a sterile aqueous solution, to give a range of final concentrations, depending on the intended use. The techniques of preparing pharmaceutical compositions are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and parity standards as required by FDA Office of Biological Standards.

In one embodiment, the present invention also encompasses a method for controlling and/or modulating the activity, expression or secretion of VEGF and/or VEGFR, preferably VEGFR-2. In another embodiment, the present invention provides a method for treating an angiogenesis-related condition using the intraceptors of the present invention, and/or a pharmaceutical composition comprising the same. Preferably, with respect to these methods of the present invention, an effective amount of the intraceptors and/or the pharmaceutical composition comprising the intraceptors of the present invention is administered to a cell or a patient that is involved in an angiogenesis-related pathology, providing a disruption of VEGF pathways for angiogenesis. In one embodiment, the intraceptors of the present invention comprise a polypeptide encoded by a polynucleotide selected from the group consisting of a polynucleotide as defined in SEQ ID NO:3 or SEQ ID NO:3, a polynucleotide encoding a polypeptide as defined in SEQ ID NO:4 or SEQ ID NO:6, and a polynucleotide complementary to a full-length polynucleotide thereof.

The present invention provides that the intraceptors can disrupt VEGF autocrine loop and in certain embodiments, can decrease corneal angiogenesis. In one embodiment, the present invention provides that the intraceptors are more effective at inhibiting corneal neovascularization than extracellular VEGF blockage such as that caused by an anti-VEGF antibody; and the intraceptors of the present invention regress corneal neovascularization. In a further embodiment, the present invention provides that one of the intraceptors, Flt24K (SEQ ID NO:6) suppresses VEGFR-2 expression and angiogenic events in human dermal microvascular endothelial cells (HMECs) by heterodimerization with VEGFR-2, thus leading to its sequestration. The present invention also provides that the intraceptor, Flt24K, can heterodimerize with VEGFR-2 after binding, with VEGF, as the full FLT receptor is known to do; such function greatly enhances its ability to disrupt intracellular autocrine loops, by entrapping both VEGF and its principal angiogenic receptor, VEGFR-2 within the endoplasmic reticulum. VEGFR-2 is the principal receptor responsible for VEGF-induced vascular endothelial cell proliferation and migration due to its strong tyrosine kinase activity.

In further preferred embodiments, the Flt23K and Flt24K intraceptor substantially inhibit and regress corneal neovascularization in vivo alter murine corneal injury.

Alternatively, the present invention also includes additional domains of FLT (SEQ ID NO:13) other than domains 2, 3, and 4 complexed with KDEL (SEQ ID NO:1), or with different endoplasmic reticulum retention sequence (e.g., HDEL (SEQ ID NO:8), RDEL (SEQ ID NO:7)). Furthermore, the present invention provides a development of an adeno- or lentivirus directing intraceptor production for sustained expression. The specificity of the intraceptors of the present invention is validated by developing alternate intraceptors to ensure that intraceptors as a group do not suppress neovascularization.

The present invention also provides different approaches to disrupt VEGF pathways intracellularly. For instance, siRNAs (short interfering RNAs) are developed, which successfully downregulate VEGF expression and inhibit and regress injury-induced corneal NV, and/or inhibit VEGFR-2 expression.

The present invention provides that accumulation of sequestered intraceptor-VEGF complexes in the endoplasmic reticulum may lead to endoplasmic reticulum, overload, triggering the unfolded protein, response (UPR), which by itself or in combination with downregulation of VEGF could cause apoptosis of endothelial cells. The presence of unfolded proteins in endoplasmic reticulum (ER) leads to a stress response, initiated by ATF6α and IRE-1 (Wang et al., 1998, EMBO J. 17:5708-17; Yoshida et al., 2001, Cell 107; 881-91; Tirasophon et al., 1998, Genes Dev. 12:1812-24), ATF6α undergoes proteolysis to p5OATF6α, a transcription factor which induces X-box binding protein 1 (XBP-1) and CHOP, which is associated with apoptosis (Fornace et al., 1988, Proc Natl Acad Set USA 85:8800-4). IRE-1, an ER transmembrane endoribonuclease and kinase, oligomerizes in the presence of ER stress, and splices XBP-1 to its active form which induces several target factors of endoplasmic reticulum associated degradation (ERAD) pathways (Wang et. al., 1998, EMBO J. 17; 5708-17; Tirasophon et at, 1998, Genes Dev. 12:1812-24) including BiP, an ER chaperone protein, and possible "master switch" In the UPR. The effect of KDEL (SEQ ID NO:1)-mediated protein retention on these molecular responses is unknown, although, it has been reported that the KDEL receptor is involved in the ER stress response (Yamamoto et al., 2003, J Biol Chem, 278:34525-32).

The present invention provides that UPR activation, by intraceptors leads to clearance of retained target proteins VEGF and VEGFR-2 by the ubiquitin-proteasome or lysosome pathways, the two key modes of clearance of accumulated proteins in the endoplasmic reticulum, providing binding of retained proteins by the ER chaperone BiP (which facilitates translocation to proteolytic compartments). The present invention characterizes the involved mechanisms of intraceptor action for the subcellular consequences of KDEL (SEQ ID NO:1)-mediated protein sequestration, and further provides opportunities for improving therapies for corneal angiogenesis or other disorders.

The present invention provides that intraceptors induce the unfolded protein response, upregulating p5OATFα, spliced XBP-1, BiP, and CHOP. In preferred embodiments, the intraceptors of the present invention induce apoptosis of vascular endothelial cells both in vitro and in viva, and that the induced apoptosis is not rescued by external VEGF due to intraceptor-induced UPR by both intraceptors and downregulation of VEGFR-2 and physiologic heterodimers by Flt24K (SEQ ID NO:6). The present invention former provides that inhibition of UPR-activated proteolytic mechanisms permits release of VEGF and VEGFR-2 from KDEL (SEQ ID NO:1) sequestration and hence decreases but not abolishes intraceptor-induced apoptosis of cells, as CHOP is also elevated by intraceptors. The present invention also provides that the ubiquitin-proteasome pathway is the principal route for clearance of intraceptor-retained proteins, as removal of KDEL (SEQ ID NO:1) from PDI, an ER chaperone, has recently been described to release its target protein, procollagen 1, from ubiquitin-proteasome degradation (Ko & Kay, 2004, Exp Cell Res 295:25-35). In one preferred embodiment, the present invention provides that disruption of normal heterodimer formation by Flt24K downregulates Ets-1, MMP-1, phosphorylation of FAK, and DNA synthesis.

ERAD (endoplasmic reticulum associated degradation) remains poorly characterized. It is generally believed that retained proteins are predominantly cleared by the proteasome or the lysosome (Ko & Kay, 2004, Exp Cell Res. 295:25-35; Hirsch et al., 2004, Biochim Biopghys Acta, 1695:208-16; Kaufman, 2002, J Clin Invest 110: 1389-98; Werner et al., 1996, Proc Natl Acad Sci 93:13979-801). Mannosidase-1 has been proposed as art enzyme In a pathway of degradation within the ER itself for misfolded glycoproteins (Kaufman, 2002, J Clin Invest 110:1389-98); both VEGF and VEGFR-2 are typically glycosylated. The present invention provides that the intraceptor activity includes proteasome or lysosome degradation of VEGF or VEGFR-2. Alternatively, the present invention provides an inhibition of mannosidase-1 with kifunensine (Hosokawa et al., 2003, J Biol Chem. 278:26287-94; Mancini et al., 2003, J Biol Chem. 278:46985-905) to demonstrate a pathway of degradation of VEGF or VEGFR-2 within, the ER itself. The present Invention also provides an expression of a plasmid expressing a mutant ubiquitin (ubiquitin-K48R), which stops polyubiquitination and protects target proteins from the proteasome (Carter et al., 2004, J. Biol Chem, 279: 52835-9).

The present invention also provides that the mechanism of intraceptor-mediated UPR activity may not lie entirely with ERAD or with CHOP induction. An early event in UPR is general downregulation of translation, mediated by PERK activation, which phosphorylates eokaryotic translation initiation factor 2 (eIF2α), which attenuates protein synthesis in all eukaryotic cells (Ko & Kay, 2004, Exp Cell Res. 295: 25-35). There is no inhibitor of eIF2α or PERK. The present invention further provides studies in PERK null mice or mice defective in eIF2α phosphorylation (Seheuoer et al., 2001, Mol Cell, 7:1165-76) to demonstrate the effects of intraceptor-mediated UPR.

The present invention also provides that alternative markers of physiologic FLT/VEGFR-2 heterodimer function can include vinculin assembly and FAK phosphorylation. Vinculin assembly can be measured in HMECs after VEGF incubation for 30 minutes and 60 minutes is detected by indirect immunofluorescence assessing for viuculin localization to areas of focal adhesion. FAK phosphorylation induced by VEGF incubation for 30 or 60 minutes is assessed, by immunoprecipitation of cell lysate using antibody to phosphotyrosine, followed by western blotting using an antibody to $p125^{FAK}$.

The present invention further provides that alternatives to apoptosis assessment include electron microscopy, TUNEL staining, staining with acridine orange/ethidium bromide, or ELISA for single-stranded DNA. The present invention also provides that an alternative to measuring effects of proteasome inhibition is evaluation of aggresome formation involving intraceptor-sequestered target proteins. Aggresomes are pericentriolar structures that accumulate ubiquitinated undegraded proteins mat are misfolded. This can be performed using immunogold labeling and transmission electron microscopy (Johnson et al., 1998, J Cell Biol 143:1883-98).

Drug delivery of potential, intraocular therapies against angiogenesis is bedeviled by potential lack of sustainability. Topical plasmids do not cross the corneal epithelial barrier, and repeated intrastromal injections are not clinically appealing. Gene therapy to date has also relied on use of viral vectors for long-term effect. These methods are plagued by virus-induced inflammation, potentiality for viral replication and infectiousness, and possible induction of oncogenesis.

The present invention provides an alternative delivery approach, the corneal electroporation. The present invention further provides that replication-deficient adenoviruses and lentiviruses are other potential long-term vectors but have disadvantages outlined above, Adeno-associated viruses are another alternative as well. Other methods for sustained delivery include use of integrase plasmids and use of the Cre-lox system.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The attention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Specific Methods
Cell Cultures

Except where indicated, the cell cultures were from ATCC, Manassas, Va.

HMECs (CDC) were grown in RPMI1640 medium supplemented with 10% fetal bovine serum (FBS) and 20 µg/mL bovine brain extract. Cells were maintained at 37° C. in 5% $CO_2$, or on 1% gelatin-coated plates in modified Kaighn's F 12K medium (ATCC) with 10% FBS, 0.03 mg/ml endothelial cell growth supplement (Sigma), and 50 U/ml heparin (Sigma).

Corneal epithelial cells (CRL-11, 515) were grown on culture-plates precoated with 0.01 mg/ml fibronectin (Sigma), 0.01 mg bovine serum, albumin (BSA) (Sigma), and 0.03 mg/ml bovine collagen type I (Vitrogen 100; Cohesion, Palo Alto, Calif.) in keratinocyte-serum free medium (ATCC) with 5 ng/ml human recombinant endothelial growth factor (EGF; Gibco, Carlsbad, Calif.), 0.05 mg/ml bovine pituitary extract (Gibco), 0.005 mg/ml insulin (Sigma), and 500 ng/ml hydrocortisone (Sigma). After passage 3, cells were used for experiments at approximately 30% confluence.

A375 cells were cultured in RPMI medium with 10% FBS, 100 units/mL penicillin, and 100 µg/mL streptomycin.

LNCaP cells were cultured In RPMI medium with 10% FBS, 100 units/mL penicillin, and 100 µg/mL streptomycin.

KG 1 cells were maintained in suspension cultures of 20% FBS and IMDM.

Hypoxia

Cells grown in 12 or 24 well culture plates were serum-starved for 12 hours, then placed in a Coy Hypoxia Chamber (Coy, Grass take, Mich.) programmed for 5% oxygen-5% carbon dioxide-90% nitrogen, which studies have shown are optimal for inducing VEGF without impairing cell viability (Namiki et al., 1995, J Biol Chem. 270:31189-95; Nomura et al. 1995, 270:28316-24). Cell culture experiments were performed in triplicate.

Vector Construction

Separate vectors were constructed containing domains 2 and 3 or 2, 3, and 4 with the ER retention signal tag linked to the end of both sequences. cDNAs encoding FLT domains 2-3 (Flt23) and domains 2, 3, 4 (Flt24) (see FIG. 1) were amplified from a corneal cDNA library (Open Biosystems). Human Rt-1 cDNA was used, as template DNA for PCR reactions (Open Biosystems). Primers were designed for the attachment of the retention signal tag to the truncated receptor sequences. Primers flt2-3 (forward) (5'-TAG GAT CCA TGG ATA CAG GTA GAC CTT TCG TAG AG-3' (SEQ ID NO:9) and flt2-3 (reverse) (5'-TAG AAT TCT ATT ACA GCT CGT CCT TTT TTC GAT GTT TCA CAG TGA-3' (SEQ ID NO:10)) were used to amplify flt2-3/KDEL (SEQ ID NO:3). Primers flt2-3 (forward) and flt2-4 (reverse) (5' TAG AAT TCT ATT ACA GCT GGT CCT TGG CCT TTT CGT AAA TCT GG-3' (SEQ ID NO:11)) .were used to amplify flt2-4/KDEL (SEQ ID NO:5). Both products were digested with EcoRI/BamHI and cloned into a pCMV vector (Stratagene, La Jolla, Calif.), creating pCMV.Flt.23K and pCMV.Flt24K. The pCMV vectors containing the modified Flt-1 clones were transfected into competent *E. coli* cells, and selected for using kanamycin antibiotics.

Model/Inducing, Labeling, and Quantitation of Corneal Neovascularization

As previously described (Ambati et al., 20002, Arch Ophthalmol 120: 1063-68), topical proparacaine and 2 μL of 0.15 M NaOH were applied to one cornea of each mouse. The corneal and limbal epithelia were removed using a Tooke corneal knife (Arista Surgical Supply, New York, N.Y.) in a rotary motion parallel to the limbus. Erythromycin ophthalmic ointment was instilled immediately following epithelial denudation.

Immunohistochemical staining for vascular endothelial cells was performed on corneal flat mounts by a masked investigator. Fresh corneas were dissected, rinsed in PBS for 30 minutes, and fixed in 100% acetone (Sigma) far 20 minutes. After washing in PBS, nonspecific binding was blocked with 0.1 M PBS, 2% albumin (Sigma) for 1 hour at room temperature. Incubation with FITC-coupled monoclonal rat anti-mouse CB31 antibody (BD Pharmingen) at a concentration of 1: 500 in 0.1 M PBS, 2% albumin at 4° C. overnight was followed by subsequent washes in PBS at room temperature. Corneas were mounted with an antifading agent (Gelmount; Biomeda, Inc; San Francisco, Calif.) and visualized with a fluorescent microscope.

Images of corneal vasculature were captured using a CD-330 charge-coupled device (CCD) camera attached to a fluorescent microscope (Proia et al., 1988, Lab Invest 58:473-79). The images were analyzed using LSM-5 Image Examiner. (Zeiss; Germany), resolved at 624×480 pixels, and converted to tagged information file format (TIFF) files. Neovascularization was quantified by setting a threshold level of fluorescence above which only vessels were captured. The entire mounted cornea was analysed in masked fashion to minimize bias. The total corneal area was outlined using the innermost vessel of the Hmbal (rim of the comes) arcade as the border. The total area of neovascularization was then normalized to the total corneal area.

Transfection of Corneal Epithelial Cells

Figure 2:
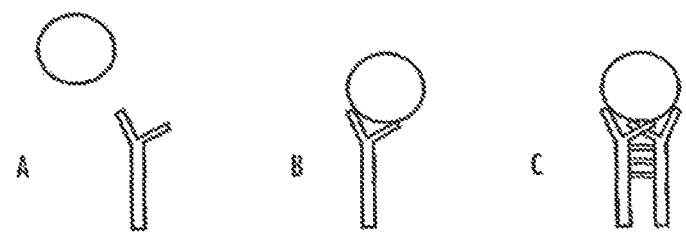
FIGS. 2A-C are schematics showing VEGF and cell membrane FLT (A) binding (B), and then heterodimerizing with cell membrane VEGFR-2 (C); the complex then activates transcription factors intracellularly.
FIGS. 2D and E are schematics illustrating cells expressing VEGF that are transfected to express Flt23K (SEQ ID NO:4) or Flt24K (both containing K.DEL(SEQ ID NO: 1) as a C-terminal tag). This will binVEGF before it is released (D) and prevent VEGF secretion. Further, in cells that also express VEGFR-2, Flt24K will then heterodimerize with VEGFR-2 as well (E). The KDEL (SEQ ID NO:1) tag will ensure retention and ultimate degradation within the endoplasmic reticulum.
Figure 2:
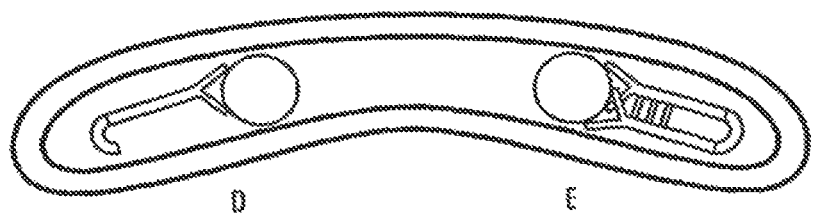

Corneal epithelial cells at 30% confluence were incubated with pCMV.Flt23K or pCMV.flt24K and transfection reagent (siPORT; Ambion, Austin, Tex.). Forty-eight hours after transfection, cells were placed in hypoxic conditions (5% $O_2$) in a hypoxia chamber (Coy Laboratory Products, Inc.). Three transfections were made per experiment. Non-transfected cells and cells transfected with empty pCMV vector served as control cultures. The former were placed in hypoxia 48 hours after reaching 30% confluence, although the latter were placed in hypoxia 48 hours after transfection. It is contemplated that tire intraceptors will interact with VEGF as shown in FIG. 2.

Immunoprecipitation

Cell lysate was diluted to 1 μg/μl total cell protein with PBS, of which 1 mg lysate was then combined with indicated antibodies and incubated overnight in 4 degrees. After 3 hours incubation at 4° C. in 20 μl washed protein G agarose bead slurry (Upstate Cell Signaling, Charlottesville, Va.), followed by microcentrifuge pulsing, agarose beads were recovered, washed 3 times in PBS, resuspended in 30 μl 2× Laemmli sample buffer, boiled for 5 minutes, and recovered again via microcentrifuge pulsing to yield supernatant for use in SDS-PAGE and immunoblot analysis.

Quantification of Corneal Neovascularization by RT-PCR

After cell harvest, RNA was isolated using Qiagen RNA isolation kits. cDNA was made using 1 μg RNA using reverse transcriptase and oligo dT primers; printers were synthesized by IDT after provision of appropriate sequences. Target RNA was amplified in 50 μL reaction mixture in a thermal cycler (Eppendorf) for 35 cycles. Amplified products were run in a 2% agarose gel.

Corneal Intrastromal Injection

Effective transfection of plasmid delivery to the cornea has been described previously (Stechschulte et al., 2001, Invest Ophthalmol Vis Sci 42:1975-79). A 30 gauge needle was used to nick the corneal stroma; a 33 gauge needle on a Hamilton syringe was passed through the nick to the center and used to inject 1.2 μg plasmid in 2 μL of solution (or 2 μL of PBS).

Harvest for ELISA

Culture medium or corneas harvested for ELISA were placed. In 60 μl lysis buffet (20 nM imidazole hydrochloride, 10 mM potassium chloride, 1 mM magnesium, chloride, 10 mM EGTA, 1% Triton X-100, 10 mM sodium fluoride, 1 mM sodium molybdate, and 1 mM EDTA (ph 6.8)), supplemented with protease inhibitor (Sigma), followed by homogenization. The lysate was cleared of debris by centrifugation at 14,000 rpm for 15 minutes (4° C.), and the supernatant was collected. Total protein was determined with a Bradford protein assay (Bio-Rad).

VEGF-ELISA

VEGF was determined by a commercially available ELISA kit (R&D Systems) that recognizes the unbound 164-amino acid splice variant of mouse VEGF. The assay was performed according to the manufacturer's instructions.

Leukocyte Counts

Two days after corneal injury, corneas were embedded in optimal cutting temperature compound, frozen in liquid nitrogen, and cut into 7 μm thick sections After fixation with ice-cold acetone and blocking with normal goat serum, sections were stained with monoclonal rat anti-mouse CD-45 (leukocyte common antigen; BD PharMingen), followed by 3,3-diaminobenzidine (DABE)-conjugated anti-rat IgG. Cells were visualised by light microscopy and counted in a masked fashion at x40. Eight consecutive serial sections were studied.

Western Blot

Corneal cell and matrix was harvested and placed in 150 μl RIPA buffer (Tris-HCL, NaCl, NP-40, Na-deoxycholate, and protease inhibitors). Immediately afterward, tissue samples were sonicated on ice four times at 15-second intervals, each at level-7 intensity. After centrifugations samples were loaded onto a 1.0% SDS-polyacrylamide gel, transferred, and probed for VEGF protein. Membranes were blocked for 1 hour at room temperature with 5% milk in PBST, followed by overnight incubations at 4° C. in a concentration of 1:1000 VEGF primary antibody (BD PharMingen), which detects unbound VEGF. The appropriate secondary antibody concentration of 1:5000 (BD PharMingen) was used to incubate the membrane for 2 hours at room temperature, after which the membrane was washed in PBST and developed on film using a chemiluminescence kit (ECL).

Statistics

Data analysis was performed on computer (Excel and SPSS for Windows). Statistical significance was assessed with Student's t-Test. Data are expressed as the mean±SEM.

Xenografts

As described (Horton et al., 1999, Canc Res 59:4064-8), athymic 6 week-old male BALB/C nu/nu mice were housed in pathogen-free conditions in laminar flow boxes; mice were imunosuppressed by irradiation with 3 Gy. One day later, one million A375 cells in 0.25 mL of culture medium were injected in upper back subcutaneously. Volumes were measured using a caliper and calculated with the formula L×W×H×0.52 (Tomayko & Reynolds, 1989, Cancer Chemother Pharmacol, 24:148-54). At harvest, mouse and tumor weight were measured to control for mouse size.

Intradermal Tumor Angiogenesis 5 days after implantation, skin encompassing the rumor site was excised and spread onto filter paper. Sections at 10× magnification were assessed for total number of vessels; the mean value of vessels in tissue from sham PBS-injected mice was subtracted from control and treated mice to better determine the treatment efficacy (Wedge et al., 2002, Cancer Res. 62:4645-55).

Adhesion

Melanoma cells labeled with calcein AM were preincubated with blocking antibodies, then stimulated by VEGF. They were transferred to wells coated with bone sialoprotein. At 1 hour, the wells were washed with DMEM by inversion, and adherent cells were quantitated by a fluorescent plate reader.

Cell Migration

Transfected cells are grown in normal medium then detached with trypsin. Cells are seeded in inner chambers of a 24-well transwell fibronectin-coated plate with 8-micron pores. In outer chambers, normal medium serves as chemoattractant. Cells are incubated for 4-6 hours, the top surface of the transwell is wiped clean, and the bottom surface stained and examined by light microscopy. Cells on the underside of the plate are quantified in 10 random, fields at 200×.

Survival

Survival of cells was tested using trypan blue exclusion assay. Trypan blue was used as a marker of cell death since dead cells are incapable of excluding this dye. For each set of cells, a light microscope was used to count the number of live and dead cells, with the minimum total number of 100 cells per set. Survival was measured as the ratio of live cells to total cells counted.

Apoptosis

For in vitro experiments, cells were collected, centrifuged, and resuspended in 1× binding buffer (10 mM Hepes/NaOH, 140 mM NaCL, 2.5 mM calcium chloride), supplemented with annexin V-FITC (BB PharMingen). After 15 minutes incubation in the dark, an excess of 1× binding buffer was added to a final volume of 0.5 mL. Cells were analysed using flow cytometry.

Caspase assay was performed after lysing cells in caspase lysis buffet and centrifuging at 8000 g for 5 minutes. One hundred mg of protein, was added to the caspase reaction buffer and 100 μM of the peptide Ac-DEVD-pNA. (Biomol Plymouth, PA). This was incubated at 37° for 4 hours and then read at 405 nm. wavelength on a spectrophotometer. Reaction buffer and peptide without lysates served as control.

For in vivo experiments, corneas were fixed in formalin and sectioned into 10 micron sections after paraffin-embedding. Sections were mounted onto slides, incubated overnight at 55° C., then deparafinized. Protein was digested with proteinase K at room temperature. After 4 washes in distilled water, endogenous peroxidase was quenched with 2% hydrogen, peroxide at room temperature and sections were washed twice in PBS. Labeling of 4'-OH fragmented DNA ends was performed with an in situ apoptosis detection kit (ApopTag, Gaithersburg, Md.) following manufacturer's instructions. Detection of labeled ends was done with kit supplied anti-digoxigenin-peroxidase antibody and development of DAB substrate.

Proliferation

MTT, a tetrazolium salt, is cleaved into a blue-colored product by active mitochondrial dehydrogenases, upregulated in proliferating cells. By colorimetrically measuring MTT before and after administration to cells, cellular metabolism is assessed. Using ELISA reader at 570 nm, proliferation is calculated as a percentage increase in absorbance compared with empty media.

DNA Synthesis 10,000 HMECs were transfected with plasmids (1.2 μg plasmid in 2 μL) directing intraceptor expression or control plasmids at 30% confluence. The cells were preincubated for 24 hours, then incubated with or without VEGF 10 ng/mL and 1.0 μCi [methyl $^3$H] thymidine (Amersham) for 24 hours. Thymidine incorporation was measured by liquid scintigraphy.

Example 2

Intraceptors Suppress VEGF Upregulation & Corneal Neovascularization in Human Corneal Epithelial (HCE) Cells A clinically relevant model of corneal neovascularization was previously established. Sodium hydroxide epithelial denudation followed by mechanical scraping consistently induces 360 degrees of neovascularization, a process driven by VEGF and its induced leukocyte recruitment (Ambati et al., 2002, Arch Ophthalmol. 120:1063-68; Amano et al., 1998, Invest Ophthalmol Vis Sci, 18-22). Angiostatin and genetic ablation of chemokine receptors CCR2 or CCR5 can partially inhibit corneal neovascularization in this model (Ambati et al., 2002, Arch Ophthalmol. 120:1063-68; Ambati et al., 2003, Invest Ophthalmol Vis Sci, 44:590-93; Ambati et al., 2003, Cornea 22:465-467).

pCMV.Flt23K and pCMV.Flt24K were generated as described in Example 1.

HCE cells were transfected at 30% confluency with pCMV.Flt23K, pCMV.Flt24K, or empty pCMV in order to confirm that VEGF is the angiogenic stimulator from hypoxia-conditioned corneal medium. 24 hours after transfection, the HCE cells were subjected to hypoxia and VEGF assays.

Figure 3A:
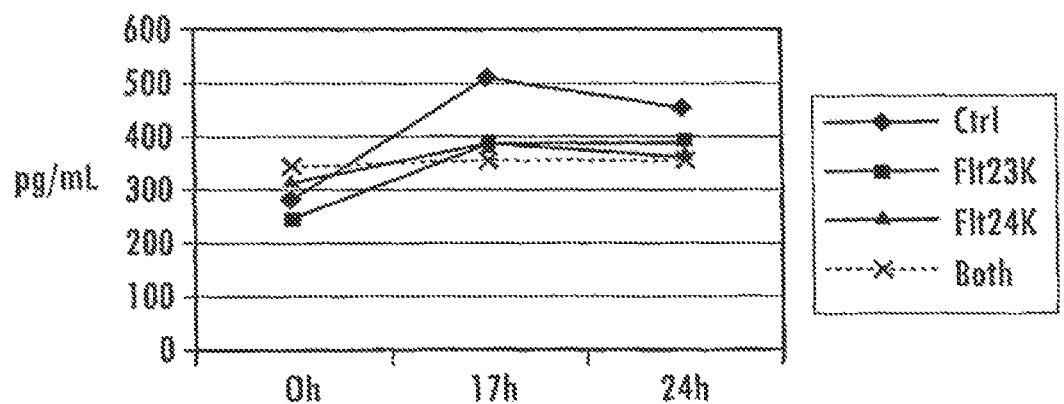
FIG. 3A shows that VEGF in hypoxic HCE cells is decreased by the presence of Flt23K (SEQ ID NO:4) and Flt24K.
Figure 3B:
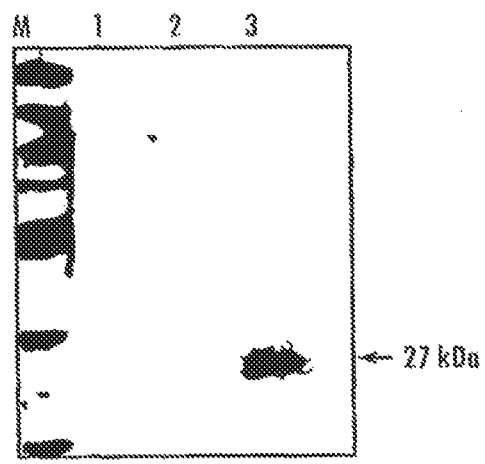
FIG. 3B shows a Western blot analysis of human corneal epithelial cell lysates. Blot analysis (anti-VEGF; 1:200) of HCEC transfected with pCMC.Flt23K (lane 1), Flt24K (lane 2), or control (lane 3). Only the control lane displayed free VEGF. Lane MW contains a standard molecular weight ladder. The beta-actin internal control was equivalent in all lanes (blots not shown).

The Flt23K and Flt24K intraceptors were found to suppress hypoxia-induced VEGF secretion in HCE cells (FIG. 3A). In control hypoxic HCE cells (experiments done in triplicate), VEGF expression in culture medium, increased from 286.8 pg/mL to 516.6 pg/mL (80.1% increase) after 17 hours of exposure to 5% oxygen and 457.6 pg/mL after 24 hours (59.6% increase over baseline). Relative to the control, pCMV.Flt23K suppressed VEGF upregulation at 17 hours (VEGF increased from 248.7 pg/mL to 389.6 pg/mL, (56.6% increase) (p=0.05)) but not at 24 hours (VEGF level of 397.9 pg/mL, 59.9% above baseline (p=0.211)). Relative to the control, pCMV.Flt24K suppressed VEGF upregulation at 17 hours (VEGF increased from 315.3 pg/mL to 398.6 pg/mL (26.4% decrease) (p=0.03)) and at 24 hours (VEGF level of 372.2 pg/mL, 18.0% above baseline) (p=0.04). The HCE cells transfected with both pCMV.Flt23K and pCMV.Flt24K had most suppression: baseline VEGF of 352.8 pg/mL rose to 363.2 pg/mL at 17 hours (2.9% increase) (p=0.01) and was 361.1 pg/mL (2.4% increase over baseline) at 24 hours (p=0.02). The loss of suppression with Flt23K at 24 hours but not Flt24K may be due to the presumed role of domain 4 in dimerization, which may enhance VEGF endoplasmic entrapment. While free VEGF was not detected in cell lysate by Western blotting (FIG. 3B), VEGF secretion (measured in the culture supernatant) was not completely suppressed; this likely indicates that intracellular sequestration is largely effective, while pre-formed stores of VEGF may have been released into extracellular space in response to hypoxia or by apoptotic or necrotic cells that release VEGF.

In summary, it has been found that VEGF secretion increases over baseline in control, cells by 80% at 17 hours and by 60% at 24 hours. However, Flt23K suppresses the increase at 17 hours by 30% (p=0.05) but does not suppress the increase at 24 hours, and Flt24K suppresses the increase at 17 hours by 73% (p=0.03) and suppresses the increase at 24h by 70% (p=0.04).

Example 3

Intraceptors Inhibit VEGF, Leukocyte Infiltration & Neovascularization Due to Corneal Injury To test the activity of VEGF intraceptors in vivo on corneal angiogenesis, and on two key angiogenesis-mediating elements; VEGF expression, and leukocyte infiltration, PBS or plasmids expressing intraceptors were intrastromally injected, using a 33 gauge Hamilton microsyringe needle. Two days later, corneal injury was performed, and one week later, corneas were harvested to quantify neovascularization. VEGF and leukocyte counts were assayed 2 days after injury. To characterize the dose-response effects of intraceptors, 0.5, 1, 2, or 4 pg of the respective plasmids were delivered into mouse cornea for inhibition and regression experimented and neovascularization, corneal VEGF levels, and leukocyte, infiltration were measured.

Figure 4A:
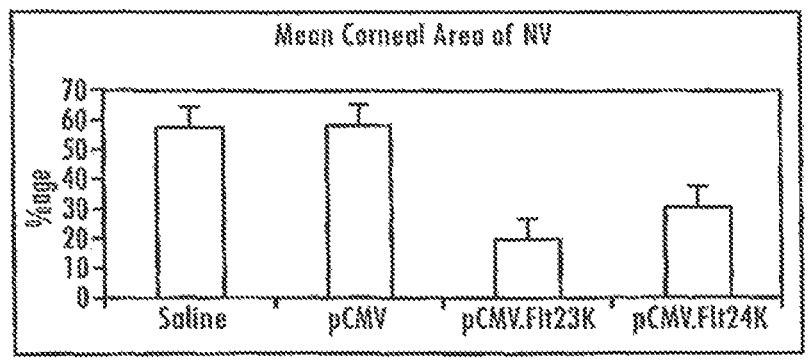
FIGS. 4A-C illustrate that injury-induced corneal neovascularization is significantly inhibited by the intraceptors of the present invention.

FIG. 4A shows the data. In mice (n=7 per subgroup), the mean percentage area±SEM of corneal neocascularization 1 week after corneal injury was 57.7±6.9% when injected with sham PBS or saline 2 days prior to injury, 58.7±7.7% in mice injected with empty pCMV (p>0.05), 19.5±6.4% in mice injected with pCMV.Flt23K (p=0.001), and 30.3±7.4% in mice injected with pCMV.Flt24K (FIG. 4A).

Figure 4B:
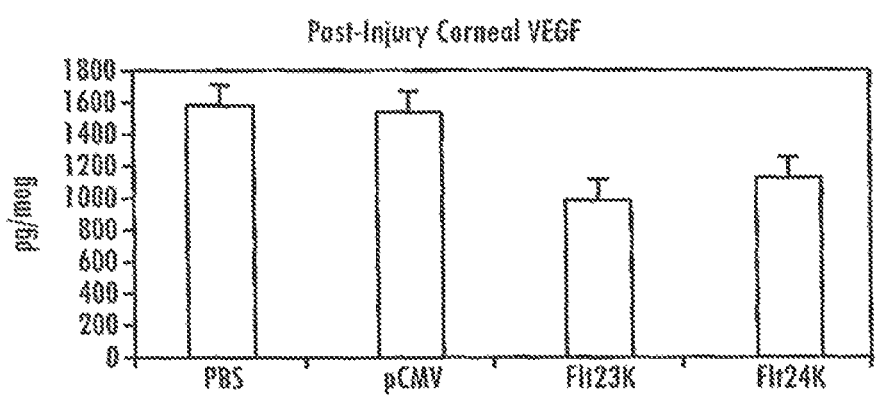
Figure 4C:
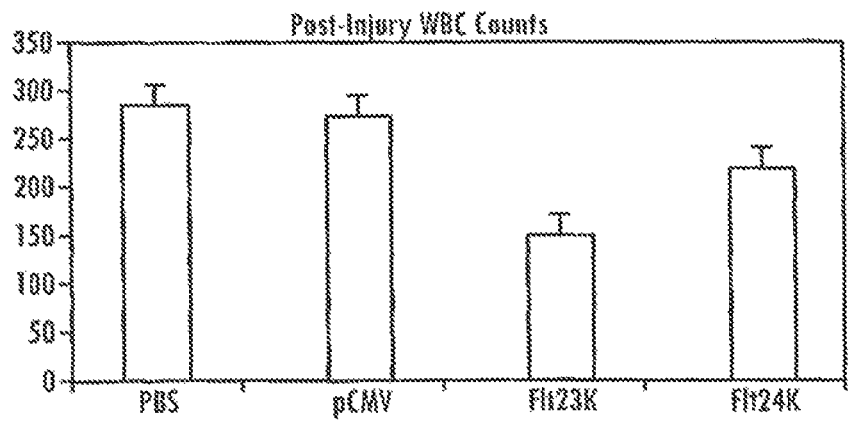

Two days after injury, corneal VEGF concentration was 1595.8±102.9 pg/µg of total protein in mice injected with PBS, 1.5.18.6±65.8 pg/µg in mice injected with empty pCMV vector, 952.2±186.0 pg/µg in mice injected with pCMV.Flt23K p=0.009), and 1119.5±152.1 pg/µg in mice injected with pCMV.Flt24K (p=0.042) (FIG. 4B). Leukocyte counts per section were 288.0±26.9 in mice injected, with PBS, 280.0±27.2 in mice injected with pCMV vector, 158.6±27.0 in mice injected with pCMV.Flt23K (p<0.001), and 206.5±27.4 in mice injected with pCMV.Flt24K (p<0.0001) (FIG. 4C).

In summary, it has found that Flt23K suppresses injury-induced corneal neovascularization by 66%, corneal VEGF expression by 37%, and corneal leukocytes infiltration by 47% (p<0.01 for all). Flt24K suppresses injury-induced corneal neovascularization by 49%, corneal VEGF expression by 37%, and corneal leukocyte infiltration by 23% (p<0.05 for all). The studies also showed no significant differences between Flt23K and Flt24K on corneal angiogenesis, VEGF expression and leukocyte infiltration.

Example 4

Intraceptor Administration Regresses Corneal Neovascularization

To determine whether intraceptors can regress corneal neovascularization, plasmids were delivered via corneal intrastromal injection 7 days after corneal injury. This time point was selected as naked plasmid expression has previously been shown to persist for 10 days and corneal neovascularization begins to plateau approximately 8 days after injury (Stechschulte et al., 2001, Invest Ophthalmol Vis Sci 42:1975-79).

Corneal injury was performed on the mice, and PBS, empty pCMV vector, pCMV.Flt23K, or pCMV.Flt24K were intrastronmally injected into their corneas 7 days later. Photographs of the corneas were taken at 7 days, 14 days, and 17 days after injury (data not shown). The data showed that pCMV.Flt23K and pCMV.Flt24K can regress corneal neovascularization. The mean percentage area of corneal neovascularization 14 days after corneal injury and 10 days after intrastromal injection was 40.4±2.7% in mice injected with empty pCMV, 23.4±7.0% in mice injected with pCMV.Flt23K (p=0.001), and 19.3±6.1% in mice injected with pCMV.Flt24K (p<0.001) (data, not shown). These data demonstrated that the intraceptors regressed corneal, neovascularization when administered after the corneal injury, and specifically demonstrate that the neovascularization at 14 days in the intraceptor-treated groups is less than the control at 14 days and at 7 days.

Example 5

Intraceptors Sequester VEGF, Suppress VEGF Secretion Induced by Hypoxia in Melanoma Cells and Flt24K binds VEGFR-2

A375 human, malignant melanoma cells (HMMCs) were known to express only VEGFR-2 and not Flt. Therefore, any results using HMMCs are not confounded by intrinsic Flt/VEGF complexes or Flt/VEGFR-2 heterodimers.

Figure 5:
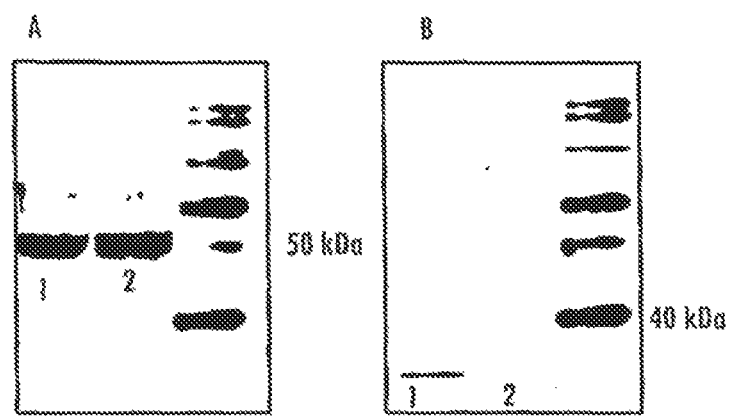
FIG. 5A shows a Western blot (anti-VEGF antibody) of HMMC cells transfected with intraceptors, grown in hypoxia 48 hours, and immunoprecipitated with anti-FLT antibody.
FIG. 5B shows a Western blot (anti-VEGFR-2 antibody) of HMMC cells transfected with, intraceptors, grows, in hypoxia 48 hours, and immunoprecipitated with anti-FLT antibody. Control cells (transfected with empty pCMV vector) did not show bands for VEGFR-2 or VEGF following immunoprecipitation for FLT (blots not shown). Lane 1: pCMV.Flt24K; Lane 2: pCMV.Flt23K.

HMMCs transfected with pCMV.Flt23K. or pCMV.Flt24K were subjected to hypoxia 48 hours after transfection. Two days later, the cellular fraction was immunoprecipitated with anti-FLT antibody (epitope specific for domains 2 and 3; Santa Cruz, Calif.) and subsequently underwent Western blotting with an anti-VEGF or an anti-VEGFR-2 antibody. A 50 kDa band (consistent with a VEGF homodimer interacting with, the intraceptor) was detected in cells transfected with pCMV.Flt23K or pCMV.Flt24K (FIG. 5A). A 30 kDa band was present in cells transfected with pCMV.Flt24K but not pCMV.Flt23K (FIG. 5B). This indicates that Flt24K can hensrodimerize with both VEGF and VEGFR-2. The isolated band Is consistent with a VEGFR-2 fragment (as it is significantly smaller than the known molecular weight of VEGFR-2 (200-220 kDa)).

Figure 6:
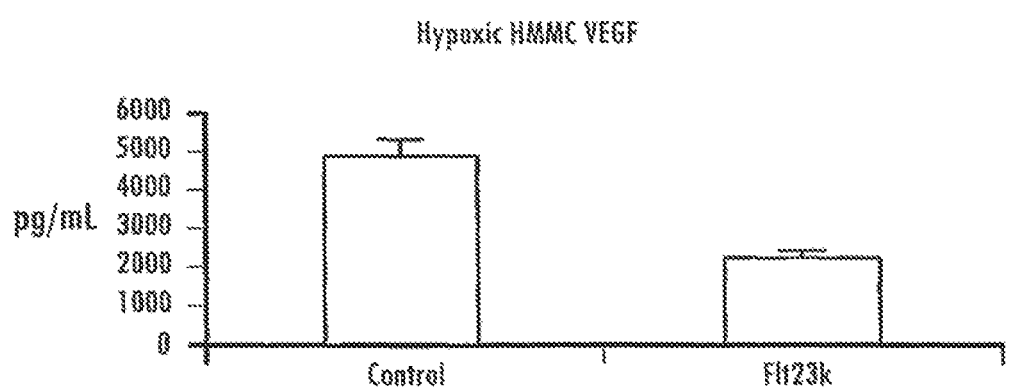
FIG. 6 illustrates that pCMV.Flt23K significantly suppresses VEGF secretion induced by hypoxia in HMMC (experiments done in triplicates; p<0.001; no significant difference in baseline VEGF levels or cell numbers).

Intraceptor suppression of VEGF secretion induced by hypoxia in HMMCs was also determined. After 72 hours of hypoxia, extracellular VEGF in the medium of control HMMCs was 4977.74±297.60 pg/ml, while that in HMMC transfected with pCMV.Flt23 one day prior to hypoxia induction was 2323.88±150.75 pg/ml (experiments done in triplicate, p<0.001; no significant difference in baseline VEGF levels or cell number) (FIG. 6).

Example 6

Intraceptor Inhibit Melanoma Xenograft Growth in Nude Mice

Figure 7A:
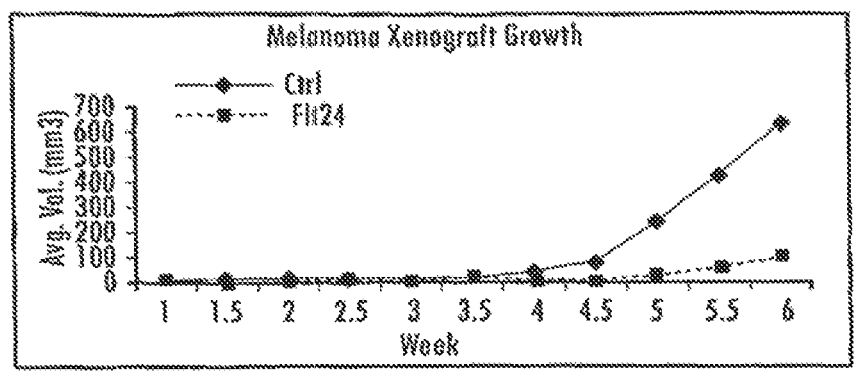
FIG. 7A illustrates that six weeks alter tumor implantation and weekly injections of either PBS or pCMV.Flt24K, HMMX xenograft sixe in nude mice was 632.8 cubic mm in control mice and 102.4 cubic mm in treated mice.
Figure 7B:
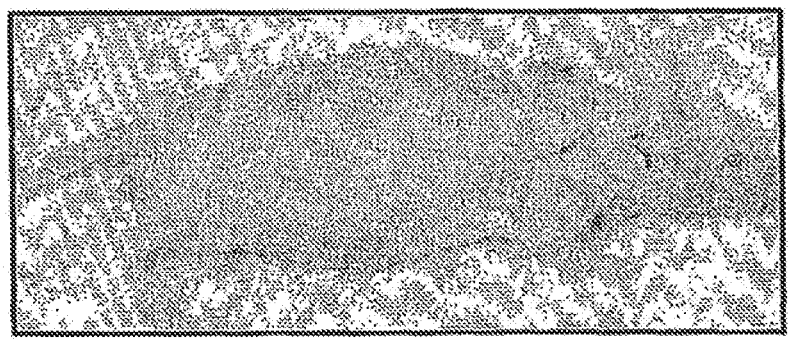
FIGS. 7B and C show representative photographs of a melanoma in a control mouse and treated, mouse, respectively.
Figure 7C:
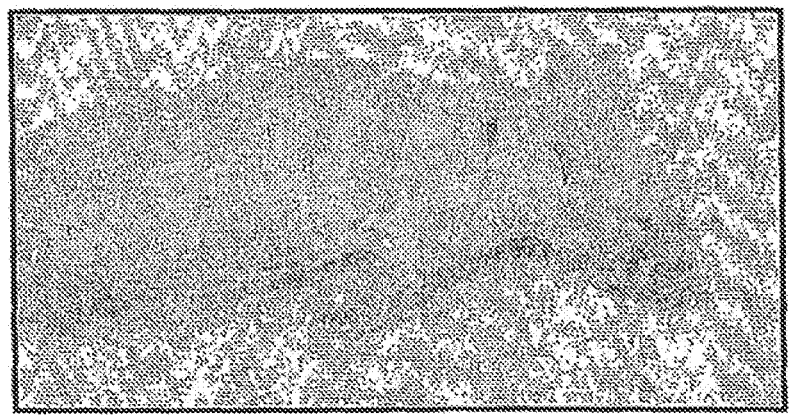

A375 xenografts were placed subcutaneously into BALB/c athymic (nude) mice. One million HMMC cells grown in vitro were injected subcutaneously in the upper dorsum of nude mice. Weekly injections of pCMV.Flt24K or control (saline) into the xenograft were administered, and tumor growth was measured biweekly. Five mice were used in each group. Flt24K (SEQ ID NO:6) was observed to dramatically suppress the growth of melanoma in this model by 83.8% over 6 weeks (FIG. 7) (p<0.001; F=19.76). Representative photographs are also shown (FIGS. 7B and C).

In further experiments, plasmids directing Flt23K (SEQ ID NO:4) or Flt24K (SEQ ID NO:6) or both are injected into the xenograft at the time of tumor placement or 7 days later, and tumor growth is evaluated, weekly for 6 weeks. Controls include empty pCMV vector and PBS. Tumor angiogenesis is assessed by microscopy to count vessels. Additionally, A375 cells are transfected with pCMV.Flt23K or pCMV.Flt24K or both (controls included PBS and empty pCMV vector). They are grown in a serum-free medium in 5% hypoxia for 48 hours, and viable cells are counted by trypan blue exclusion, using a hemacytometer. Apoptosis is assessed by using TUNEL staining or caspase 3 levels. VEGFR-2 expression is assessed by flow cytometry, and VEGF secretion is also assessed by ELISA. Immunohistochemistry is used to determine colocalization of intraceptors with VEGF and VEGFR-2 in the endoplasmic reticulum to verify success of this approach in melanoma cells. Adhesion is assessed by adherence to bone sialoprotein, and migration by transwell plates. To assess whether the presumed autocrine loops are intracellular, the control groups includes cells treated with neutralizing anti-VEGF monoclonal antibodies or extracellular soluble VEGFR-1.

Example 7

Alkali-Mechanical Trauma Does Not Induce Significant Lymphangiogenesis

To determine whether lymphangiogenesis is a significant component in the model of corneal neovascularization induced by alkali-mechanical trauma, vessels were labeled with rabbit anti-mouse LVYE-1, a lymphatic marker, 10 days after corneal injury. A minimal lymphangiogenesis (<10% of corneal area compared to ~60% for hemangiogenesis) was found (data not shown).

Example 8

Figure 8:
FIG. 8 shows a Western blot with anti-XBP-1 of hypoxic HMEC cells showing that intraceptors of the present invention upregulate spliced XBP-1 (MW of visible band in land 3 and 4 is about 55 kD). Beta-actin internal control was equivalent in all lanes (blots not shown) . . . Lane 1=PBS; 2=empty pCMV; 3=pCMV.Flt23K; 4=pCMV.Flt24K.

Intraceptors induce the Formation of Spliced XBP-1 in Vitro and in Vivo and Induce CHOP The unfolded protein response (UPR) induces conversion, of the constitutive 30 kD form of X-box binding protein 1 (XBP-1) through alternative splicing to its active 55 kDa form, which induces endoplasmic reticulum associated degradation of sequestered proteins. To determine whether intraceptors induce the UPR, HMECs were transfected with pCMV.Flt23K or pCMV.Flt24K. Controls included empty pCMV and PBS. Twenty-four hours after transfection, cells were placed in 5% hypoxia for 6 hours, and cell lysates were analysed by Western blotting with anti-XBP-1 antibody (Chemicon). The 55 kDa spliced variant of XBP-1 was upregulated in cells transfected with intraceptors, consistent with an induction of the UPR (FIG. 8).

Figure 9:
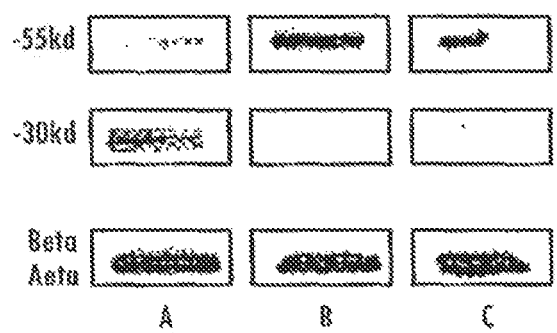
FIG. 9 shows a Western blot showing expression of the 30 kDa form of XBP-1 in control corneas, and elevation of the active 55 kDa form in corneas injected with plasmids expressing the intraceptors of the present invention. Lane A shows mouse corneas injected, with empty pCMV vector; Lane B shows mouse corneas injected with pCMV.Flt23K; and Lane C shows mouse corneas injected with pCMV.Flt24K.

For the in vivo study, corneal injury was performed, and 10 days later, empty pCMV, pCMV.Flt23K, or pCMV.Flt24K was intrastromally injected. Mouse corneas were harvested 2 days later and Western. blotting was performed for XBP-1 (experiments in triplicate; FIG. 9). The intraceptors promoted the conversion of the inactive form of XBP-1 to its active form (FIG. 9). These data suggested that accumulation of sequestered intraceptor-VEGF complexes in the endoplasmic reticulum might lead to endoplasmic reticulum overload, triggering the unfolded protein response (UPR), which by itself or in combination with downregulation of VEGF could cause apoptosis of endothelial cells.

Figure 10:
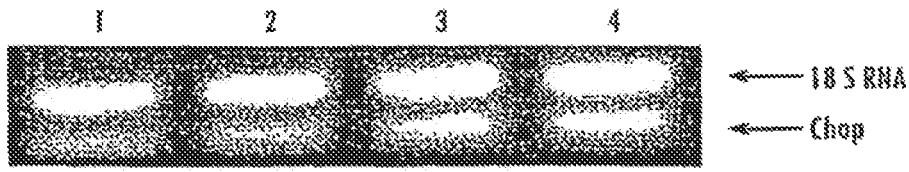

In addition to XBP-1 splicing, the UPR induces CHOP, which is associated with apoptosis. To test whether intraceptor delivery would elevate CHOP, HMECs were transfected with pCMV.Flt23K and pCMV.Flt24K, in vitro and RT-PCR for CHOP expression was performed 24 hours later (experiments in triplicate). It was found that intraceptors induce elevation of CHOP levels (FIG. 10).

In vivo expression of the intraceptors in the cornea is cornea by R.T-PCR and Western blot.

To determine whether intraceptors are more successful, at inhibiting corneal angiogenesis than extracellular VEGF blockade, plasmids expressing intraceptors or insert slow-release EVA copolymer pellets containing 10 pg anti-VEGF antibody (a dose sufficient to block extracellular VEGF) are delivered into a corneal pocket One day later, corneal neovascularization is induced by combined mechanical-alkali trauma. Corneal VEGF levels are assessed 2 days later and corneal neovascularization 1 week later.

To determine whether intraceptors induce apoptosis and trigger the UPR, plasmids expressing pCMV.Flt23K or pCMV.Flt24K are transfected in HMECs. Empty pCMV vector and reagent alone are transfected as controls. After 3 days of incubation, cell proliferation, is assessed using the MTT assay with ELISA, survival by trypan blue exclusion, and apoptosis by annexin V staining and caspase-3 ELISA. After 1 day of incubation, UPR activation is assessed by assessing levels of p5OATF6α, spliced XBP-1, BiF, and CHOP by Western blot and RT-PCR. To further determine whether apoptosis is due to the ER stress-induced UPR or to mere down regulation of VEGF, VEGF (10 ng/mL) is added to the culture medium of cells, as this would be expected to rescue cells from the latter but not the former. To confirm that UPR activation is specifically directed towards retained VEGF or VEGFR-2, immunoprecipitation is performed with anti-BiP antibody (Santa Cruz) and Western blotting with antibodies to VEGF or VEGFR-2. These experiments are carried out both in normoxic and 5% hypoxic-conditions.

To further characterize whether apoptosis is due to UPR-induced proteolysis of VEGF or to CHOP induction, plasmids expressing pCMV.Flt23K or Flt24IC are transfected in HMEC, with the same controls as above. One day later, UPR-activated proteolytic mechanisms are inhibited using 10 pM of MG132 (potent inhibitor of both, ubiquitin-proteasome pathway and lysosomes), lactacystin (inhibitor of proteasomes) and chioroquine (inhibitor of lysosomes). The UPR-activated proteolytic mechanisms are known to be the predominant mechanism of protein, digestion in ERAD (Ko & Kay, 2004: Exp Cell Res. 295:25-35).

The effect of proteasome inhibition is measured by assessing accumulation of ubiquitinated VEGF or VEGFR-2 through immunoprecipitation with anti-VEGF or and VEGFR-2 antibody followed by Western blot with anti-ubiquitin antibody. The effect of lysosome inhibition, is measured by assessing accumulation of VEGF or VEGFR-2 in the Golgi complex by double immunostaining with anti-Golgi 58k protein antibody and anti-VEGF or VEGFR-2 antibody (Ko & Kay, 2004, Exp Cell Res. 295:25-35). To determine whether proteolytic blockade may allow escape of sequestered proteins from UPR into the medium or cell surface, VEGF secretion and VEGFR-2 levels are measured by ELISA and flow cytometry, respectively, after 12 hours.

To assess the role of CHOP in inducing apoptosis in this study, a plasmid expressing an siRNA against CHOP is developed and co-transfect into HMECs along with plasmids expressing intraceptors. Apoptosis is assessed 24 hours later using above-noted methods. To further define whether apoptosis is due primarily to endoplasmic reticular stress, procaspase 12 expression is assessed by ELISA, as caspase 12 activation is specific to apoptosis induced by endoplasmic reticular stress (Kaufman, 2002, J Clin Invest. 110; 1389-98; Schroder & Kaufman, 2005, Mutat Res. 560:29-63). These experiments are carried out both in normoxic and 5% hypoxic conditions.

To determine whether intraceptors suppress cellular events normally mediated by physiologic FLT/VEGFR-2 heterodimers, plasmids expressing pCMV.Flt24K are transfected in HMEC, with controls as above. One day after transfection the cells are incubated with VEGF (10 ng/mL). After 4 hours of incubation, cells are harvested for RT-PCR analysis of Ets-1 and MMP-1. DNA synthesis is assessed by incubating cells with VEGF and tritiated-methyl thymidine and measuring incorporation of the latter after 24 hours by liquid scintigraphy.

To determine whether intraceptors induce apoptosis in vivo, based on the methods described above, corneal neovascularization is induced by combined mechanical-alkali trauma. pCMV.Flt23K and pCMV.Flt24K are delivered via corneal intrastromal injection 7 days after corneal injury; controls are PBS and empty pCMV vector that were delivered as well. At 10, 15, and 20 days after injury, apoptosis is assessed by performing dual labeling with CD31 and annexin V immunostaining on corneas. Ghost vessels are identified by using dual-immunolabeling with antibodies to collagen IV and CD31 (a ghost vessel would be positive for collagen IV but not CD31, while the corneal stroma, where vessels generally are present, normally does not have collagen IV (Baluk et at, 2003, Am J Path. 163; 1801-15).

To determine the effects of intraceptors on corneal neovascular endothelium, corneal neovessel endothelial ($CD31^+$ $CD45^-$) cells are isolated by magnetic cell sorting of neovascularized corneal cell suspensions yielded by collagenase digestion to analyze intracellalar events (unfolded protein response markers, heterodimerization-induced events, apoptosis-related markers) specifically in these cells. Mouse choroidal macrophages are previously isolated using magnetic cell sorting Yoshida et al., 1997, Mol Cell Biol. 17; 4015-23). MMP-1, XBP-1, p50ATF6, and CHOP expression is assessed by Western blotting in uninjured corneas, then, at 4, 8, 12, and 16 days after injury (as expected, these markers of intraceptor activity precede apoptosis) in both whole corneas by Western blotting and from corneal neovessel endothelial cells by RT-PCR.

What is claimed is:

1. A method of treating an angiogenesis-related condition in a patient, comprising:

administering to a cell of the patient involved in the angiongenesis-related condition a nucleic acid encoding a chimeric polypeptide comprising domains 2 and 3 of VEGFR-1 (Flt) operatively linked to an endoplasmic reticulum signal retention peptide, wherein the nucleic acid comprises SEQ ID No. 3.

2. The method of claim 1, wherein the patient is a human.

3. The method of claim 1, wherein the angiogenesis-related condition is selected from the group consisting of inflammation, stroke, hemangioma, solid tumors, leukemias, lymphomas, myelomas, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, fractures, keloids, vasculogenesis, hematopoiesis, ovulation, menstruation, placentation, polycystic ovary syndrome, dysfunctional uterine bleeding, endometrial hyperplasia and carcinoma, endometriosis, failed implantation and subnormal foetal growth, myometrial fibroids (uterine leiomyomas) and adenomyosis, ovarian hyperstimulation syndrome, ovarian carcinoma, melanoma, venous ulcers, acne, rosacea, warts, eczema, neurofibromatosis, tuberous sclerosis, and chronic inflammatory disease.

4. The method of claim 1, wherein the angiogenesis-related condition is selected from the group consisting of melanoma, diabetic retinopathy, and macular degeneration.

5. The method of claim 1, further comprising coupling the nucleic acid to a regulatory sequence suitable for expression in a human cell.

* * * * *